(12) United States Patent
Shiono et al.

(10) Patent No.: US 8,304,163 B2
(45) Date of Patent: *Nov. 6, 2012

(54) COMPOUND, DISSOLUTION INHIBITOR, POSITIVE TYPE RESIST COMPOSITION, AND METHOD OF FORMING RESIST PATTERN

(75) Inventors: Daiju Shiono, Kawasaki (JP); Taku Hirayama, Kawasaki (JP); Toshiyuki Ogata, Kawasaki (JP); Shogo Matsumaru, Kawasaki (JP); Hideo Hada, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 43 days.

This patent is subject to a terminal disclaimer.

(21) Appl. No.: 12/980,914

(22) Filed: Dec. 29, 2010

(65) Prior Publication Data

US 2011/0091810 A1  Apr. 21, 2011

Related U.S. Application Data

(63) Continuation of application No. 11/911,341, filed as application No. PCT/JP2006/308080 on Apr. 17, 2006, now Pat. No. 7,943,284.

(30) Foreign Application Priority Data

Apr. 15, 2005 (JP) ................................ 2005-118724
Oct. 13, 2005 (JP) ................................ 2005-298385

(51) Int. Cl.
*G03F 7/004* (2006.01)
(52) U.S. Cl. ..................................... 430/270.1; 430/905
(58) Field of Classification Search ............... 430/270.1, 430/905
See application file for complete search history.

(56) References Cited

U.S. PATENT DOCUMENTS

| 6,638,684 B2 | 10/2003 | Okubo et al. |
| 6,787,284 B2 | 9/2004 | Ogata et al. |
| 2001/0041302 A1 | 11/2001 | Kim et al. |
| 2007/0275328 A1 | 11/2007 | Shiono et al. |

FOREIGN PATENT DOCUMENTS

| EP | 1736485 A | 12/2006 |
| JP | 2006-78744 | 3/2006 |
| KR | 10-2001-0083547 | 9/2001 |
| WO | WO 2004/051372 A2 | 6/2004 |

OTHER PUBLICATIONS

Office Action that issued in the counterpart Korean Application No. 10-2009-7013172, dated Aug. 28, 2009.
Office Action that issued in the counterpart Korean Application No. 10-2007-7023160, dated Jan. 23, 2009.
Hirayama, T., et al. "New Photoresist Based on Amorphous Low Molecular Weight Polyphenols," Journal of Photopolymer Science and Technology (2004) vol. 17, No. 3. p. 435-440.
International Search Report from PCT/JP2006f308080 dated Jul. 11, 2006.
Kim, J., et al. "Novel Molecular Resist Based on Derivative of Cholic Acid." Chemistry Letters (2002), vol. 31, No. 10, pp. 1064-1065, Figure 1.

*Primary Examiner* — John Chu
(74) *Attorney, Agent, or Firm* — Knobbe Martens Olson & Bear LLP

(57) ABSTRACT

A positive type resist composition for forming a high resolution resist pattern and a method of forming a resist pattern are provided which use a low-molecular-weight material as a base component, and a compound and a dissolution inhibitor that are each suitable for the positive type resist composition. Here, the compound is a non-polymer having a molecular weight of 500 to 3000, and is decomposed under the action of an acid to produce two or more molecules of a decomposition product having a molecular weight of 200 or more; the dissolution inhibitor comprises the compound; the positive type resist composition comprises the compound and the acid generator component; and the method of forming a resist pattern uses the positive type resist composition.

1 Claim, 1 Drawing Sheet

COMPOUND, DISSOLUTION INHIBITOR, POSITIVE TYPE RESIST COMPOSITION, AND METHOD OF FORMING RESIST PATTERN

RELATED APPLICATIONS

This application is a continuation of U.S. application Ser. No. 11/911,341, filed Oct. 11, 2007, which is the US National Phase entry under 35 USC §371 of PCT/JP2006/308080, filed Apr. 17, 2006, which claims priority to Japanese Patent Application No. 2005-118724, filed on Apr. 15, 2005 and Japanese Patent Application No. 2005-298385, filed on Oct. 13, 2005, the contents of which are herein incorporated by reference.

TECHNICAL FIELD

The present invention relates to a positive type resist composition, a method of forming a resist pattern using the positive type resist composition, and a compound and a dissolution inhibitor which are each suitably used for the positive type resist composition.

BACKGROUND ART

In recent years, along with the progress made in lithography techniques in the preparation of semiconductor devices or liquid crystal display devices, formation of ultrafine patterns has been increasingly required.

With this trend of formation of ultrafine patterns, the wavelengths of the exposure sources also have tended to become shorter. Specifically, as the exposure source, ultraviolet rays such as g-ray and i-ray have been conventionally used, but currently, distribution of a semiconductor device using the KrF excimer laser or the ArF excimer laser is started. Furthermore, an $F_2$ excimer laser that has a shorter wavelength than the above-mentioned excimer lasers, an electron beam, an EUV (extreme ultraviolet) ray, an X-ray, or the like are under investigation.

As one of the pattern forming materials for forming a pattern with a fine dimension, there is known a chemically amplified resist having a base component having film formability, and an acid generator component that generates an acid upon light exposure. The chemically amplified resists can be classified into two types, that is, a negative type, in which alkali solubility is reduced upon light exposure, and a positive type, in which alkali solubility is enhanced upon light exposure.

Conventionally, as the base component of the chemically amplified resist, there have been used a polymer, including polyhydroxy styrene (PHS), or a PHS-based resin in which a part of the hydroxyl groups of the PHS have been protected with an acid-dissociable, dissolution-inhibiting groups, a copolymer derived from a (meth)acrylic acid ester, or a resin in which a part of the carboxylic groups of the copolymer have been protected with an acid-dissociable, dissolution-inhibiting groups.

However, when a pattern is formed by using the above pattern forming materials, there arises a problem of roughness occurrence on the top surface or side wall surface of the pattern. For example, the roughness on the side wall surface of the resist pattern, that is, line edge roughness (LER) causes distortions around the holes in the hole pattern, or irregularities in the line width in the line-and-space pattern, which may produce an adverse effect on the formation of a fine semiconductor device.

The problem of the roughness becomes more severe as the pattern dimension is lessened. However, the polymer which is generally used as a base has a molecular size as large as several nm (root mean square radius per one molecule). In the developing process for the formation of a pattern, the dissolution behavior of the resist in the developer is typically analyzed in terms of one molecule unit of the base component, and as a result, as long as the polymer is used as the base component, it is extremely difficult to further reduce the roughness.

Under these circumstances, there has been proposed a resist using a low-molecular-weight material as a base component in order to provide extremely low roughness. For example, Non-Patent Documents 1 and 2 each propose a low-molecular-weight material containing an alkali-soluble group such as a hydroxyl group, and a carboxylic group, in which a part or all of the groups have been protected with an acid-dissociable, dissolution-inhibiting groups.

[Non-Patent Document 1] T. Hirayama, D. Shiono, H. Hada, and J. Onodera: J. Photopolym. Sci. Technol. 17 (2004), p. 435

[Non-Patent Document 2] Jim-Baek Kim, Hyo-Jin Yun, Young-Gil Kwon: Chemistry Letters (2002), p. 1064~1065

DISCLOSURE OF THE INVENTION

Problems that the Invention is to Solve

It is expected that such a low-molecular-weight material will reduce the roughness due to its low molecular weight and small molecular size. However, even with the use of the low-molecular-weight material, sometimes a high resolution resist pattern having a practically usable level, such as a fine pattern of 200 nm or less, may not be obtained. For example, there may be a problem in that the pattern itself cannot be formed, or the pattern, if formed, has a low resolution.

It is an object of the present invention to provide a positive type resist composition forming a high resolution resist pattern and a method of forming a resist pattern, using a low-molecular-weight material as a base component, and a compound and a dissolution inhibitor that are each suitable for the positive type resist composition.

Means for Solving the Problems

In a first embodiment of the present invention to accomplish the above-mentioned object, there is provided a compound (A1) which is a non-polymer having a molecular weight of 500 to 3000, and is decomposed under the action of an acid to give two or more molecules of a decomposition product having a molecular weight of 200 or more.

In a second embodiment of the present invention, there is provided a dissolution inhibitor which contains the compound according to the first embodiment.

In a third embodiment of the present invention, there is provided a positive type resist composition comprising a base component (A) which increases its own alkali solubility through the action of an acid, and an acid generator component (B) which generates an acid upon irradiation with radiation, in which the base component (A) contains a compound (A1) that is a non-polymer having a molecular weight of 500 to 3000, and is decomposed under the action of an acid to give two or more molecules of a decomposition product having a molecular weight of 200 or more.

In a fourth embodiment of the present invention, there is provided a method of forming a resist pattern, which includes the steps of forming a resist film on a substrate using the positive type resist composition according to the third embodiment, exposing the resist film, and developing the resist film to form a resist pattern.

Furthermore, as used herein, the term "(light) exposure" is meant to encompass general processes for irradiation with radiation.

The term "organic group" includes a group containing a carbon atom, but may contain other atoms than a carbon atom (for example, a hydrogen atom, an oxygen atom, a nitrogen atom, a sulfur atom, and a halogen atom (a fluorine atom, a chlorine atom, etc.), or the like.

The "alkyl group" is meant to include a straight-chained, branched, and cyclic, saturated mono-valent hydrocarbon group, unless otherwise specified.

The "alkylene group" is meant to include a straight-chained, branched, and cyclic, saturated di-valent hydrocarbon group, unless otherwise specified.

Advantages of the Invention

According to the present invention, there can be provided a positive type resist composition for forming a high resolution resist pattern, and a method of forming a resist pattern, using a low-molecular-weight material as a base component, and a compound and a dissolution inhibitor that are each suitable for the positive type resist composition.

BEST MODE FOR CARRYING OUT THE INVENTION

<Compound>

Figure 1:
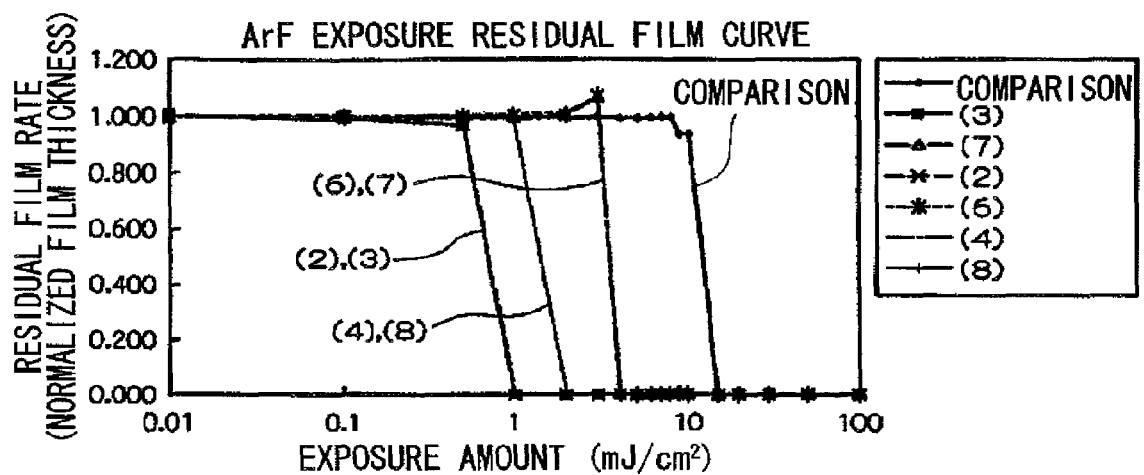
FIG. 1 is a curve of the residual film after ArF exposure, showing the change in the residual film rate at varying exposure amounts of ArF excimer laser in the positive type resist composition including the compound of the present invention.

The compound of the present invention (referred to as compound (A1), hereinafter) is a non-polymer having a molecular weight of 500 to 3000, and is decomposed under the action of an acid to give two or more molecules of a decomposition product having a molecular weight of 200 or more.

As used herein, the term "non-polymer" means a substance which is not a polymer, and the term "polymer" is a compound which is obtained by polymerization of one or more monomers, and consists of a plurality of repeating units (constituent units).

The compound (A1) has a molecular weight of preferably 500 to 2500, more preferably 500 to 2000, and still more preferably 500 to 1600. With a molecular weight of 500 or more, the compound has good film formability, thereby leading to formation of a resist film. On the other hand, with a molecular weight of 3000 or less, the compound can form a high resolution resist pattern. In addition, the roughness of the formed resist pattern is reduced, thereby obtaining a good profile form.

Furthermore, for the effect of the present invention, the compound (A1) is required to be decomposed under the action of an acid to give two or more molecules of a decomposition product having a molecular weight of 200 or more, preferably 2 to 4 molecules of a decomposition product having a molecular weight of 200 or more.

The upper limit of the molecular weight of the decomposition product varies depending on the molecular weight, etc. of the compound (A1), but is preferably 1000 or less, and more preferably 900 or less. If the upper limit is 1000 or less, the compound (A1) has a good ability to form a high resolution resist pattern.

As such, the compound (A1) having a specific range of the low-molecular-weight is decomposed into a plurality of decomposition products having a molecular weight of a specific limit or more, thereby obtaining the effect of the present invention. It is believed that this is caused by the uniformity of the compound (A1).

Specifically, a conventional resist including a high molecular-weight-polymer (resin) as a base component hardly regulates the molecular weight distribution or alkali solubility distribution. For this reason, there are limitations in the reduction of LFR, or the like due to its distribution or its molecular size.

Furthermore, the low-molecular-weight compound considered to be used for solving the above-described problem still has the same problem as above in that protection of the alkali-soluble groups with an acid-dissociable, dissolution-inhibiting groups causes variance in the positions and protection rates of the protected alkali-soluble groups, and as a result, variance in its properties, as described in Non-Patent Documents 1 and 2, etc.

On the other hand, the compound (A1) is a non-polymer, and does not need to have its alkali-soluble groups protected with an acid-dissociable, dissolution-inhibiting groups, like a resin used in a conventional chemically amplified positive type resist, or the low-molecular-weight compounds as proposed in Non-Patent Documents 1 and 2, etc., and as a result, it has a definite structure and uniform molecular weight. Thus, it has uniformity in the properties such as alkali solubility, hydrophilicity, and hydrophobicity, and as a result, it can form a resist film having uniform properties.

Furthermore, in such a resist film, the compound (A1) is decomposed under the action of an acid which has been generated upon light exposure, thereby increasing its alkali solubility. However, even after such a decomposition, a remarkably high-molecular-weight compound does not remain, and relatively, the difference in the molecular weights of generated decomposition products becomes lower. Accordingly, the decomposition product is also uniformly distributed in the resist film, and the difference in the dissolution behaviors of the decomposition products for alkali developers is also low. As such, it is believed that the compound (A1) can form a resist film having uniform properties before and after light exposure, thereby obtaining the effects of the present invention.

Furthermore, the compound (A1) is required to be a material for forming an amorphous film by a spin-coating method. As used herein, the amorphous film means an optically transparent film which does not crystallize. The spin-coating method is one of the means that are generally used for forming a thin film, and it can be determined whether the compound is a material capable of forming an amorphous film by a spin-coating method, on the basis of whether all the surfaces of the film formed on an 8-inch silicon wafer by a spin-coating method are transparent. More specifically, it can be determined in the following manner. First, a solvent that is generally used for a resist solvent is used to dissolve the compound. For example, 100 parts by mass of the compound (A1) is dissolved in 1570 parts by mass of an organic solvent of propylene glycol monomethyl ether acetate, and ultrasonic treatment (dissolution treatment) is performed for dissolution using an ultrasonic cleaner. The solution is spin-coated on a wafer at 1500 rpm, and optionally subject to PAB (Post Applied Bake) at 110° C. for 90 seconds, and then it is determined whether an amorphous film is formed by observing with the naked eye whether it is transparent. Here, a film that is not transparent is not an amorphous film.

In the present invention, by using the compound (A1), preferably the amorphous film formed above has good stability, and for example, the amorphous state of the film is maintained even after being left to stand at room temperature for 2 weeks after the PAB treatment.

Specific examples of the compound (A1) include the compound represented by the following general formula (A-1) or (A-2) (referred to as the compound (A1-1), hereinafter).

The compound (A1-1) has the following structure, and accordingly if it is combined with, for example, an acid generator component in a positive type resist composition, the linkage between the oxygen atom bound to the carbon atom of the carbonyl group adjacent to, $R^3$ to $R^4$, and $R^9$ and $R^{10}$, and the carbon atom (the carbon atom bound to $R^1$ and $R^2$, $R^5$ to $R^8$, etc.) bound to the oxygen atom is dissociated and decomposed under the action of the acid generated from the acid generator component upon exposure. By such decomposition, the molecular weight is reduced, and carboxylic acids such as $R^3$—COOH and $R^4$—COOH are generated as the decomposition products, thereby increasing the alkali solubility in the exposed area. For this, by performing alkali developing, a positive type resist pattern can be formed.

For example, for the compound represented by the following general formula (A-1), it is believed that (n+1) carboxylic acids (one $R^3$—COOH and n $R^4$—COOH) generated by the decomposition of the terminal portion, and one compound derived from a core portion (a portion including X, etc.) are generated as the decomposition products. Furthermore, for the compound represented by the following general formula (A-2), it is believed that (n'+1) carboxylic acids (one $R^9$—COOH and n' $R^{10}$—COOH) generated by the decomposition of the terminal portion, and one compound derived from a core portion (a portion including Y, etc.) are generated as the decomposition products. In the present invention, at least two decomposition products should have a molecular weight of 200 or more, and in particular, all of the carboxylic acids preferably have a molecular weight of 200 or more.

[Chemical Formula 1]

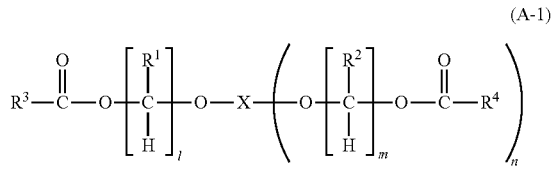

(A-1)

(where $R^1$ and $R^2$ are each independently a hydrogen atom, a halogen atom, an alkyl group, or a halogenated alkyl group; $R^3$ and $R^4$ are each independently a group containing a polycyclic group, or a group containing at least two cyclic groups including at least one monocyclic group; l and m are each independently an integer of 1 to 3; n is an integer of 1 to 3; and X is an (n+1)-valent organic group)

[Chemical Formula 2]

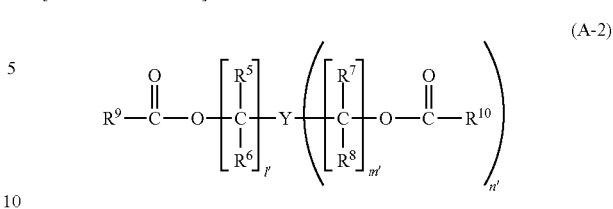

(A-2)

(where $R^5$ to $R^8$ are each independently an alkyl group or a halogenated alkyl group; $R^9$ and $R^{10}$ are each independently a group containing a polycyclic group, or a group containing at least two cyclic groups including at least one monocyclic group; l', and m' are each independently an integer of 1 to 3; n' is an integer of 1 to 3; and Y is an (n'+1)-valent organic group)

In the general formula (A-1), $R^1$ and $R^2$ are each independently a hydrogen atom, a halogen atom, an alkyl group, or a halogenated alkyl group.

Examples of the halogen atom include a fluorine atom, a chlorine atom, a bromine atom, and an iodine atom, and among these, a fluorine atom is particularly preferred.

The alkyl group of $R^1$ and $R^2$ is not particularly limited, and examples thereof include a straight-chained, branched, or cyclic alkyl group having 1 to 10 carbon atoms. The alkyl group is preferably a straight-chain or branched, lower alkyl group having 1 to 5 carbon atoms, or a cyclic alkyl group having 5 to 6 carbon atoms. Examples of the straight-chain or branched, lower alkyl group include a methyl group, an ethyl group, a propyl group, an isopropyl group, an n-butyl group, an isobutyl group, a tert-butyl group, a pentyl group, an isopentyl group, and a neopentyl group. Examples of the cyclic alkyl group include a cyclohexyl group and a cyclopentyl group.

Examples of the halogenated alkyl group include an alkyl group, in which part or all of the hydrogen atoms of the above-mentioned alkyl groups have been substituted with halogen atom (s).

$R^1$ and $R^2$ are particularly preferable hydrogen atoms.

$R^3$ and $R^4$ are each a group containing a polycyclic group, or a group containing at least two cyclic groups including at least one monocyclic group.

For $R^3$ to $R^4$, the decomposition product including $R^3$ or $R^4$, among the decomposition products generated by the decomposition of the compound (A1-1), preferably has a molecular weight of 200 or more. That is, $R^3$—COOH and $R^4$—COOH are generated as the decomposition products generated by the decomposition of the compound (A1-1), and $R^3$—COOH and $R^4$—COOH preferably has a molecular weight of 200 or more.

The polycyclic group may be an aromatic polycyclic group, or an aliphatic polycyclic group, but among these, an aliphatic polycyclic group is preferred in terms of exerting the excellent effects of the invention. As used throughout the claims and specification, the term "aliphatic" refers to a concept relative to the term aromatic, and is defined as a group or compound that is not aromatic. The expression "aliphatic polycyclic group" refers to a polycyclic group that is not aromatic.

The polycyclic group may or may not have a substituent. Examples of the substituent include a lower alkyl group having 1 to 5 carbon atoms, a fluorine atom, a fluorinated lower alkyl group having 1 to 5 carbon atoms, that has been substituted with a fluorine atom, an oxygen atom (=O), and a hydroxyl group.

Examples of the "aromatic polycyclic group" include an aromatic polycyclic group having 10 to 16 carbon atoms. Specific examples thereof include groups in which one hydrogen atom has been removed from naphthalene, anthracene, phenanthrene, pyrene, or the like. Specific examples include a 1-naphthyl group, a 2-naphthyl group, a 1-anthracenyl group, a 2-anthracenyl group, a 1-phenanthryl group, a 2-phenanthryl group, a 3-phenanthryl group, and a 1-pyrenyl group.

The structure of the basic ring from which the substituent of the "aliphatic polycyclic group" has been removed is not limited to the group consisting of carbon and hydrogen (a hydrocarbon group), but the hydrocarbon group is preferred. The hydrocarbon group may be saturated or unsaturated, but usually is preferably saturated. Specific examples of the aliphatic cyclic group include a group in which at least one hydrogen atom has been removed from a polycycloalkane such as bicycloalkane, tricycloalkane, and tetracycloalkane. Specific examples include groups in which at least one hydrogen atom has been removed from a polycycloalkane such as adamantane, norbornane, isobornane, tricyclodecane, and tetracyclododecane.

The "group containing a polycyclic group" may be the polycyclic group as described above, or a group containing the polycyclic group as a substituent.

Examples of the group containing the polycyclic group as a substituent include a group in which the hydrogen atom of a straight-chained or branched alkyl group has been substituted with the polycyclic group. As used herein, the straight-chained or branched alkyl group is preferably an alkyl group having 1 to 10 carbon atoms, more preferably an alkyl group having 1 to 8 carbon atoms, and most preferably an alkyl group having 1 to 5 carbon atoms.

$R^3$ and $R^4$ may be the same as or different from each other, but preferably the same as each other in terms of exerting the excellent effects of the invention, and ease of synthesis.

In the present invention, $R^3$ and $R^4$ are particularly each preferably a group having a perhydrocyclopentaphenanthrene ring on its backbone in terms of exerting the excellent effects of the invention.

The perhydrocyclopentaphenanthrene ring is a condensed polycyclic hydrocarbon consisting of three 6-membered rings and one 5-membered ring, as shown in the following formula, and is known to constitute the backbone of steroids such as bile acid and cholesterol.

[Chemical Formula 3]

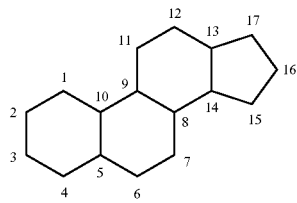

The perhydrocyclopentaphenanthrene ring may have a substituent such as a lower alkyl group having 1 to 5 carbon atoms, a fluorine atom, a fluorinated lower alkyl group having 1 to 5 carbon atoms, that has been substituted with a fluorine atom, an oxygen atom (=O), and a hydroxyl group, and particularly among these, a methyl group and/or a hydroxyl group is/are preferred in terms of industrial availability.

As the group having the perhydrocyclopentaphenanthrene ring on its backbone, a group in which a carboxylic group has been removed from cholanic acid, or a monocarboxylic acid having a ring backbone of the cholanic acid, bonded with a substituent such as a hydroxyl group and an oxygen atom (=O) is preferred, and particularly, a group in which a carboxylic group has been removed from at least one monocarboxylic acid selected from the group consisting of cholanic acid, lithocholic acid, deoxycholic acid, cholic acid, α-hyodeoxycholic acid, and dehydrocholic acid is further preferred in terms of industrial availability.

For the group containing at least two cyclic groups including at least one monocyclic group as $R^3$ to $R^4$, the monocyclic group may be an aromatic monocyclic group or an aliphatic monocyclic group, but among these, an aromatic monocyclic group is preferred in terms of exerting the excellent effects of the invention. Examples of the aromatic monocyclic group include a group in which at least one hydrogen atom has been removed from benzene.

The monocyclic group may or may not have a substituent. Examples of the substituent include an aryl group having 6 to 14 carbon atoms, a lower alkyl group having 1 to 5 carbon atoms, a fluorine atom, a fluorinated lower alkyl group having 1 to 5 carbon atoms, that has been substituted with a fluorine atom, an oxygen atom (=O), and a hydroxyl group, and particularly, among these, a methyl group and/or a hydroxyl group is/are preferred in terms of industrial availability.

The group containing at least two cyclic groups including at least one monocyclic group may have a polycyclic group. Examples of the polycyclic group include those as exemplified above.

In the present invention, the group containing at least two cyclic groups including at least one monocyclic group as $R^3$ and $R^4$ is preferably a group containing at least two aromatic monocyclic groups, and particularly preferably a group containing three aromatic monocyclic groups.

Among these, a group having a triphenylmethane backbone in which three hydrogen atoms of methane have been substituted with phenyl groups is preferred. As for this group, the phenyl group may have a substituent such as a lower alkyl group and a hydroxyl group.

l and m are each independently an integer of 1 to 3, preferably 1 or 2, and most preferably 1.

n is an integer of 1 to 3, preferably 1 or 2, and most preferably 1.

Furthermore, if n is an integer of 2 or more, that is, if the compound (A1) has two or more groups represented by $R^4$—COO—$[C(R^2)H]_m$—O—, these groups may be the same as or different from each other.

X is an (n+1)-valent organic group.

For X, the organic group is preferably a straight-chained, branched, or cyclic, saturated hydrocarbon group, and more preferably a straight-chained or branched, saturated hydrocarbon group. The saturated hydrocarbon group preferably has 1 to 15 carbon atoms, more preferably 1 to 10 carbon atoms, and still more preferably 1 to 6 carbon atoms.

The saturated hydrocarbon group may or may not have a substituent. The substituent is not particularly limited, and examples thereof include a halogen atom such as a fluorine atom, a chlorine atom, a bromine atom, and an iodine atom, and a straight-chained, branched, or cyclic alkyl group having 1 to 6 carbon atoms. As used herein, the expression "having a substituent" means that part or all of the hydrogen atoms of the saturated hydrocarbon group are substituted with substituents.

Furthermore, examples of X include a group in which part of the carbon atoms of the above-described saturated hydrocarbon groups are substituted with a heteroatom such as an oxygen atom, a nitrogen atom, and a sulfur atom.

X is preferably a saturated di-valent or tri-valent hydrocarbon group, and particularly a di-valent alkylene group. The saturated hydrocarbon group may be straight-chained, branched, or cyclic.

Examples of the straight-chained or branched saturated tri-valent hydrocarbon group include a group in which three hydrogen atoms have been removed from methane, ethane, propane, butane, pentane, hexane, heptane, octane, or the like.

Examples of the cyclic saturated tri-valent hydrocarbon group include a cyclic group in which three hydrogen atoms have been removed from a saturated hydrocarbon ring such as cyclopentane, cyclohexane, cycloheptane, norbornane, isobornane, adamantane, tricyclodecane, and tetracyclodecane, and a group in which a straight-chained or branched alkylene group has been bound to the group.

Examples of the straight-chained or branched alkylene group include a methylene group, an ethylene group, a propylene group, an isopropylene group, an n-butylene group, an isobutylene group, a tert-butylene group, a pentylene group, an isopentylene group, and a neopentylene group.

Examples of the cyclic alkylene group include a group in which two hydrogen atoms have been removed from a saturated hydrocarbon ring such as cyclopentane, cyclohexane, norbornane, isobornane, adamantane, tricyclodecane, and tetracyclodecane, and a group in which a straight-chained or branched alkylene group has been bound to the group.

X is preferably a straight-chained or branched alkylene group, more preferably straight-chained alkylene group, and particularly an ethylene group or a propylene group.

In the general formula (A-2), examples of the alkyl group and the halogenated alkyl group as $R^5$ to $R^8$ include the same as those mentioned for the alkyl groups and the halogenated alkyl groups as $R^1$ and $R^2$ in the general formula (A-1). Furthermore, $R^9$ and $R^{10}$ in the general formula (A-2) include the same as those mentioned for $R^3$ and $R^4$ in the general formula (A-1).

Furthermore, examples of l', m', n', and Y include the same as those mentioned for l, m, n, and X in the general formula (A-1), respectively.

The compound (A1-1) can be synthesized, for example, by dissolving a monocarboxylic acid (such as cholanic acid, lithocholic acid, deoxycholic acid, cholic acid, α-hyodeoxycholic acid, dehydrocholic acid, adamantane monocarboxylic acid, norbornane monocarboxylic acid, tricyclodecane monocarboxylic acid, and tetracyclodecane monocarboxylic acid) containing a polycyclic group in a solvent such as tetrahydrofuran, and reacting it with a bischloro-compound represented by the following general formula (a-1) or (a-2) in the presence of a catalyst such as triethylamine.

[Chemical Formula 4]

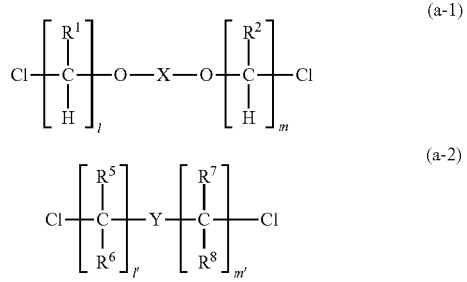

(where $R^1$ and $R^2$, $R^5$ to $R^8$, X, Y, l, m, l', and m' are each the same as defined above)

<Dissolution Inhibitor>

The compound (A1) of the present invention can be suitably used as the dissolution inhibitor of the positive type resist composition. By using the dissolution inhibitor comprising the compound (A1) of the present invention, the alkali solubility of the resist film (before exposure) obtained by using the positive type resist composition including the dissolution inhibitor is suppressed. Accordingly, when the resist film is selectively exposed, the difference between the alkali solubility of the exposed area and that of the unexposed (dissolution contrast) is increased, thereby forming a resist pattern having good resolution or shape.

The dissolution inhibitor of the present invention can be used by adding it to a two-component chemically amplified resist composition that includes a resin component containing an acid-dissociable, dissolution-inhibiting groups and an acid generator component, or by adding it to a three-component chemically amplified resist composition that includes a resin component containing no acid-dissociable, dissolution-inhibiting groups, an acid generator component, and a dissolution inhibitor of the present invention.

<Positive Type Resist Composition>

The positive type resist composition of the present invention includes a base component (A) that contains an acid-dissociable, dissolution-inhibiting groups, and increases the alkali solubility under the action of an acid (sometimes referred to as the component (A), hereinafter), and an acid generator component (B) that generates an acid upon light exposure (sometimes referred to as component (B), hereinafter).

For the component (A), under the action of acid generated from the acid generator component (the component (B)) upon exposure, the acid-dissociable, dissolution-inhibiting groups dissociates, causing the entire component (A) to change from an alkali-insoluble state to an alkali-soluble state. Thus, in the formation of a resist pattern, if the resist film including the positive type resist composition is selectively exposed, or if heating is additionally performed after the exposure, the exposed area changes to an alkali-soluble state, while the unexposed area remains in an alkali-insoluble state. Accordingly, by performing alkali developing, a positive type resist pattern can be formed.

[Component (A)]

In the positive type resist composition of the present invention, the component (A) is required to include a compound (A1) which is a non-polymer having a molecular weight of 500 to 3000, and is decomposed under the action of an acid to give two or more molecules of a decomposition product having a molecular weight of 200 or more, that is, the compound (A1) of the present invention.

The compound (A1) may be used alone, or in combination of two or more kinds thereof.

The proportion of the compound (A1) in the component (A) is preferably more than 40% by mass, more preferably more than 50% by mass, still more preferably more than 80% by mass, and most preferably 100% by mass.

The proportion of the compound (A1) in the component (A) can be measured by using a means such as reverse phase chromatography.

The component (A) may include further any resin component (sometimes referred to as the component (A2), hereinafter), that has been conventionally suggested as a base component for a chemically amplified resist layer, within the range that does not interfere with the effects of the present invention.

Examples of the component (A2) include those conventionally suggested as a base resin for a chemically amplified positive type resist composition for KrF, a positive type resist composition for ArF, or the like, and the component (A2) can be suitably selected according to the kind of the exposure source that is used upon formation of a resist pattern.

The content of the component (A) in the positive type resist composition of the present invention can be adjusted according to the thickness of the resist film to be formed.

[Component (B)]

The component (B) is not particularly limited in kind, and examples of the component (B) include those that have been suggested as an acid generator for a chemically amplified resist. As the acid generator, there have been conventionally known an onium salt-based acid generator such as an iodonium salt and a sulfonium salt; an oxime sulfonate-based acid generator; a diazomethane-based acid generator such as bis-alkyl or bisaryl sulfonyl diazomethanes, and poly(bisulfonyl) diazomethanes; a nitrobenzyl sulfonate-based acid generator; an iminosulfonate-based acid generator; a disulfone-based acid generator; and the like.

Examples of the onium salt-based acid generator include the compounds represented by the following general formula (b-1) or (b-2).

[Chemical Formula 5]

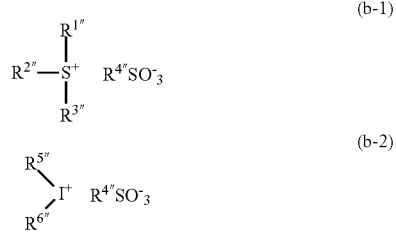

(where $R^{1''}$ to $R^{3''}$, and $R^{5'''}$ to $R^{6'''}$ each independently represents an aryl group or an alkyl group; $R^{4''}$ represents a straight-chained, branched, or cyclic alkyl group or a fluorinated alkyl group; at least one of $R^{1''}$ to $R^{3''}$ represents an aryl group, and at least one of $R^{5'''}$ to $R^{6'''}$ represents an aryl group)

In the formula (b-1), $R^{1''}$ to $R^{3''}$ each independently represents an aryl group or an alkyl group. At least one of $R^{1''}$ to $R^{3''}$ represents an aryl group. Preferably, at least two of $R^{1''}$ to $R^{3''}$ represent an aryl group, and most preferably all of $R^{1''}$ to $R^{3''}$ represent an aryl group.

The aryl group of $R^{1''}$ to $R^{3''}$ is not particularly limited, and examples thereof include an aryl group having 6 to 20 carbon atoms, and part or all of the hydrogen atoms of the aryl group may be unsubstituted or substituted with an alkyl group, an alkoxy group, a halogen atom, or the like. The aryl group is preferably an aryl group having 6 to 10 carbon atoms in terms of low cost for synthesis. Specific examples of the aryl group include a phenyl group and a naphthyl group.

The alkyl group with which the hydrogen atom of the aryl group may be substituted is preferably an alkyl group having 1 to 5 carbon atoms, and most preferably a methyl group, an ethyl group, a propyl group, an n-butyl group, or a tert-butyl group.

The alkoxy group with which the hydrogen atom of the aryl group may be substituted is preferably an alkoxy group having 1 to 5 carbon atoms, and most preferably a methoxyl group, or an ethoxy group.

The halogen atom with which the hydrogen atom of the aryl group may be substituted is preferably a fluorine atom.

The alkyl group of $R^{1''}$ to $R^{3''}$ is not particularly limited, and examples thereof include a straight-chained, branched, or cyclic alkyl group having 1 to 10 carbon atoms. The alkyl group having 1 to 5 carbon atoms is preferred in terms of high resolution. Specific examples of the alkyl group include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. A methyl group is preferred in terms of high resolution and low cost for synthesis.

Among these, most preferably $R^{1''}$ to $R^{3''}$ are all phenyl groups.

$R^{4''}$ represents a straight-chained, branched, or cyclic alkyl group, or a fluorinated alkyl group.

The straight-chained alkyl group preferably has 1 to 10 carbon atoms, more preferably 1 to 8 carbon atoms, and most preferably 1 to 4 carbon atoms.

The cyclic alkyl group is a cyclic group as represented by $R^{1''}$ as above, and it preferably has 4 to 15 carbon atoms, and more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. The fluorination rate of the fluorinated alkyl group (the proportion of the fluorine atoms in the alkyl group) is preferably 10 to 100%, still more preferably 50 to 100%, and particularly those in which all of the hydrogen atoms have been substituted with fluorine atoms, thus giving strong acidity, are preferred.

$R^{4''}$ is most preferably a straight-chained or cyclic alkyl group, or a fluorinated alkyl group.

In the formula (b-2), $R^{5'''}$ and $R^{6'''}$ each independently represents an aryl group or an alkyl group. At least one of $R^{5'''}$ and $R^{6'''}$ represents an aryl group. Preferably, all of $R^{5'''}$ and $R^{6'''}$ are each an aryl group.

Examples of the aryl group of $R^{5'''}$ and $R^{6'''}$ include those as described for the aryl group of $R^{1''}$ to $R^{3''}$.

Examples of the alkyl group of $R^{5'''}$ and $R^{6'''}$ include those as described for the alkyl group of $R^{1''}$ to $R^{3''}$.

Among these, most preferably $R^{5'''}$ and $R^{6'''}$ are all phenyl groups.

Examples of $R^{4''}$ in the formula (b-2) include those as described for $R^{4''}$ in the formula (b-1).

Specific examples of the onium salt-based acid generator include diphenyliodonium trifluoromethanesulfonate or nonafluorobutanesulfonate, bis(4-tert-butylphenyl) iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl) sulfonium trifluoromethanesulfonate, heptafluoropropanesulfonate or nonafluorobutanesulfonate, dimethyl(4-hydroxynaphthyl) sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methyl phenyl) diphenylsulfonium trifluoromethanesulfonate, heptafluoropropanesulfonate or nonafluorobutanesulfonate, (4-methoxyphenyl) diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, diphenyl(1-(4-methoxy) naphthyl) sulfonium trifluoromethanesulfonate, heptafluoropropanesulfonate or nonafluorobutanesulfonate, and the like. Also, onium salts in which the anionic part of those onium salts are substituted with methanesulfonate, n-propanesulfonate, n-butanesulfonate, or n-octanesulfonate can be used.

In the general formula (b-1) or (b-2), those in witch the anionic part is substituted with the anionic part represented by the following general formula (b-3) or (b-4) can also be used (the cationic part is the same as for (b-1) or (b-2)).

[Chemical Formula 6]

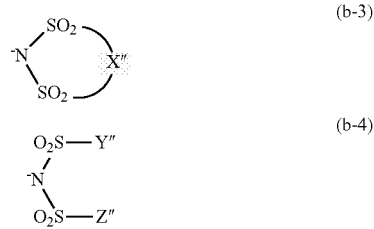

(where X" represents an alkylene group having 2 to 6 carbon atoms in which at least one hydrogen atom has been substituted with a fluorine atom; Y" and Z" each independently represents an alkyl group having 1 to 10 carbon atoms in which at least one hydrogen atom has been substituted with a fluorine atom)

X" is a straight-chain or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Y" and Z" are each independently a straight-chain or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

Smaller number of carbon atoms of the alkylene group of X", or of the alkyl group of Y" and Z" are better in terms of solubility in a resist solvent.

Furthermore, larger numbers of the hydrogen atoms substituted with a fluorine atom in the alkylene group of X", or in the alkyl group of Y" and Z" are better in terms of stronger acidity, and higher transparency to high-energy light at 200 nm or less, or an electron beam. The proportion of the fluorine atoms in the alkylene group or alkyl group, that is, the fluorination rate is preferably 70 to 100%, still more preferably 90 to 100%, and a perfluoroalkylene group or perfluoroalkyl group in which all of the hydrogen atoms are substituted with fluorine atoms is particularly preferred.

In the present invention, the oxime sulfonate-based acid generator is a compound having at least one group represented by the following general formula (B-1), which is characterized by generation of an acid upon irradiation with radiation. The oxime sulfonate-based acid generator is widely used for a chemically amplified resist composition, and thus can be optionally selected and used.

[Chemical Formula 7]

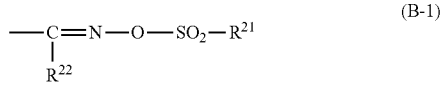

(where $R^{21}$ and $R^{22}$ each independently represents an organic group)

The organic group of $R^{21}$ and $R^{22}$ is a carbon atom-containing group, and may contain atoms other than the carbon atom (for example, a hydrogen atom, an oxygen atom, a nitrogen atom, a sulfur atom, and a halogen atom (such as a fluorine atom, and a chlorine atom)).

The organic group of $R^{21}$ is preferably a straight-chained, branched, or cyclic alkyl group or an aryl group. The alkyl group or the aryl group may have a substituent. The substituent is not particularly limited, and examples thereof include a fluorine atom, and a straight-chained, branched, or cyclic alkyl group having 1 to 6 carbon atoms. As used herein, the expression "having a substituent" means that part or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, particularly preferably 1 to 6 carbon atoms, and most preferably 1 to 4 carbon atoms. The alkyl group is particularly preferably a partially or completely halogenated alkyl group (sometimes referred to as the halogenated alkyl group, hereinafter). Furthermore, the partially halogenated alkyl group refers to an alkyl group in which part of the hydrogen atoms are substituted with halogen atoms, and the completely halogenated alkyl group refers to an alkyl group in which all of the hydrogen atoms are substituted with halogen atoms. Examples of the halogen atom include a fluorine atom, a chlorine atom, a bromine atom, and an iodine atom. It is particularly preferably a fluorine atom. That is, the halogenated alkyl group is preferably a fluorinated alkyl group.

The aryl group preferably has 4 to 20 carbon atoms, more preferably 4 to 10 carbon atoms, and most preferably 6 to 10 carbon atoms. The aryl group is particularly preferably a partially or completely halogenated aryl group. Furthermore, the partially halogenated aryl group refers to an aryl group in which part of the hydrogen atoms are substituted with halogen atoms, and the completely halogenated aryl group refers to an aryl group in which all of the hydrogen atoms are substituted with halogen atoms.

$R^{21}$ is particularly preferably an unsubstituted alkyl group having 1 to 4 carbon atoms, or a fluorinated alkyl group having 1 to 4 carbon atoms.

The organic group of $R^{22}$ is preferably a straight-chained, branched, or cyclic alkyl group, an aryl group, or a cyano group. Examples of the alkyl group and the aryl group of $R^{22}$ include those as described for the alkyl group and the aryl group of $R^{21}$.

$R^{22}$ is particularly preferably an unsubstituted alkyl group having 1 to 8 carbon atoms, or a fluorinated alkyl group having 1 to 8 carbon atoms.

More preferable examples of the oxime sulfonate-based acid generator include the compounds represented by the following general formula (B-2) or (B-3).

[Chemical Formula 8]

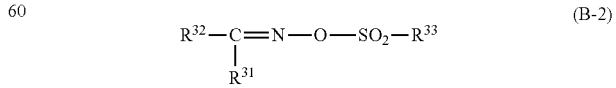

(where $R^{31}$ is a cyano group, an unsubstituted alkyl group, or a halogenated alkyl group; $R^{32}$ is an aryl group; and $R^{33}$ is an unsubstituted alkyl group or a halogenated alkyl group)

[Chemical Formula 9]

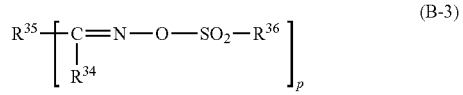

(where $R^{34}$ is a cyano group, an unsubstituted alkyl group, or a halogenated alkyl group; $R^{35}$ is a di or tri-valent aromatic hydrocarbon group; $R^{36}$ is an unsubstituted alkyl group, or a halogenated alkyl group; and p is 2 or 3)

In the general formula (B-2), the unsubstituted alkyl group or the halogenated alkyl group of $R^{31}$ preferably has 1 to 10 carbon atoms, more preferably 1 to 8 carbon atoms, and most preferably 1 to 6 carbon atoms.

$R^{31}$ is preferably a halogenated alkyl group, and more preferably a fluorinated alkyl group.

The fluorinated alkyl group of $R^{31}$ is preferably one in which 50% or more of the hydrogen atoms of the alkyl group are fluorinated, more preferably one in which 70% or more of the hydrogen atoms of the alkyl group are fluorinated, and most preferably one in which 90% or more of the hydrogen atoms of the alkyl group are fluorinated.

Examples of the aryl group of $R^{32}$ include a group in which one hydrogen atom has been removed from the ring of an aromatic hydrocarbon such as a phenyl group, a biphenyl group, a fluorenyl group, a naphthyl group, an anthracyl group, and a phenanthryl group; and a heteroaryl group in which part of the carbon atoms constituting those rings are substituted with a heteroatom such as an oxygen atom, a sulfur atom, and a nitrogen atom. Among these, a fluorenyl group is preferred.

The aryl group of $R^{32}$ may have a substituent such as an alkyl group having 1 to 10 carbon atoms, a halogenated alkyl group, and an alkoxy group. The alkyl group or the halogenated alkyl group as the substituent preferably has 1 to 8 carbon atoms, and more preferably 1 to 4 carbon atoms. Furthermore, the halogenated alkyl group is preferably a fluorinated alkyl group.

The unsubstituted alkyl group or the halogenated alkyl group of $R^{33}$ preferably has 1 to 10 carbon atoms, more preferably 1 to 8 carbon atoms, and most preferably 1 to 6 carbon atoms.

$R^{33}$ is preferably a halogenated alkyl group, more preferably a fluorinated alkyl group, and most preferably a partially fluorinated alkyl group.

The fluorinated alkyl group of $R^{33}$ is preferably one in which 50% or more of the hydrogen atoms of the alkyl group are fluorinated, more preferably one in which 70% or more of the hydrogen atoms of the alkyl group are fluorinated, and most preferably one in which 90% or more of the hydrogen atoms of the alkyl group are fluorinated in terms of higher acidity of an acid generated. Most preferably, it is one in which 100% of the hydrogen atoms of the alkyl group are completely fluorinated.

In the general formula (B-3), examples of the unsubstituted alkyl group or the halogenated alkyl group of $R^{34}$ include those as described above for the unsubstituted alkyl group or the halogenated alkyl group of $R^{31}$.

Examples of the di- or tri-valent aromatic hydrocarbon group of $R^{35}$ include a group in which one or two hydrogen atoms are removed from the aryl group of $R^{32}$.

Example of the unsubstituted alkyl group or the halogenated alkyl group of $R^{36}$ include those as described above for the unsubstituted alkyl group or the halogenated alkyl group of $R^{33}$.

P is preferably 2.

Specific examples of the oxime sulfonate-based acid generator include α-(p-toluenesulfonyloxyimino)-benzylcyanide, α-(p-chlorobenzenesulfonyloxyimino)-benzylcyanide, α-(4-nitrobenzenesulfonyloxyimino)-benzylcyanide, α-(4-nitro-2-trifluoromethylbenzenesulfonyloxyimino)-benzylcyanide, α-(benzenesulfonyloxyimino)-4-chlorobenzylcyanide, α-(benzenesulfonyloxyimino)-2,4-dichlorobenzylcyanide, α-(benzenesulfonyloxyimino)-2,6-dichlorobenzylcyanide, α-(benzenesulfonyloxyimino)-4-methoxybenzylcyanide, α-(2-chlorobenzenesulfonyloxyimino)-4-methoxybenzylcyanide, α-(benzenesulfonyloxyimino)-thien-2-ylacetonitrile, α-(4-dodecylbenzenesulfonyloxyimino)-benzylcyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienylcyanide, α-(methylsulfonyloxyimino)-1-cyclopentenylacetonitrile, α-(methylsulfonyloxyimino)-1-cyclohexenylacetonitrile, α-(methylsulfonyloxyimino)-1-cycloheptenylacetonitrile, α-(methylsulfonyloxyimino)-1-cyclooctenylacetonitrile, α-(trifluoromethylsulfonyloxyimino)-1-cyclopentenylacetonitrile, α-(trifluoromethylsulfonyloxyimino)-cyclohexylacetonitrile, α-(ethylsulfonyloxyimino)-ethylacetonitrile, α-(propylsulfonyloxyimino)-propylacetonitrile, α-(cyclohexylsulfonyloxyimino)-cyclopentylacetonitrile, α-(cyclohexylsulfonyloxyimino)-cyclohexylacetonitrile, α-(cyclohexylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, α-(n-butylsulfonyloxyimino)-1-cyclohexenylacetonitrile, α-(methylsulfonyloxyimino)-phenylacetonitrile, α-(methylsulfonyloxyimino)-p-methoxyphenylacetonitrile, α-(trifluoromethylsulfonyloxyimino)-phenylacetonitrile, α-(trifluoromethylsulfonyloxyimino)-p-methoxyphenylacetonitrile, α-(ethylsulfonyloxyimino)-p-methoxyphenylacetonitrile, α-(propylsulfonyloxyimino)-p-methylphenylacetonitrile, and α-(methylsulfonyloxyimino)-p-bromophenylacetonitrile.

Furthermore, examples of the oxime sulfonate-based acid generator include the compounds represented by the following formulae.

[Chemical Formula 10]

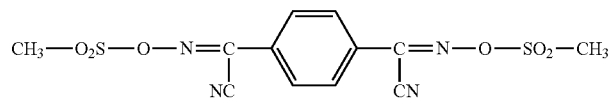

-continued
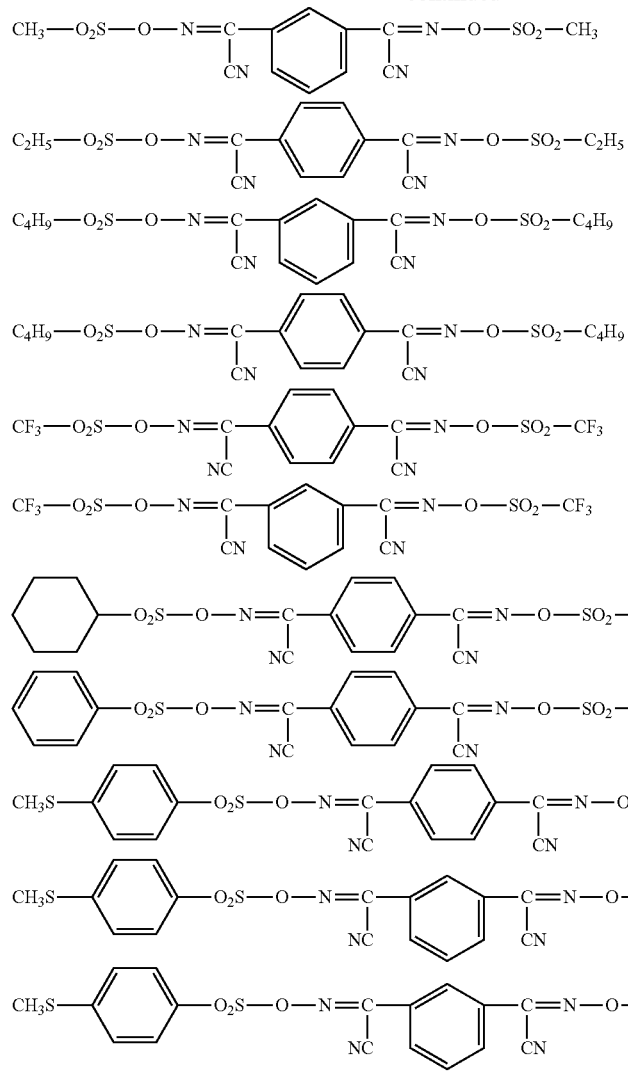
Examples of the preferable compounds, among the compounds represented by the above-described general formula (B-2) or (B-3), are as follows.
[Chemical Formula 11]
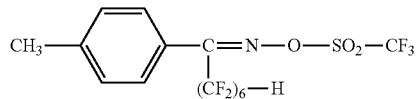
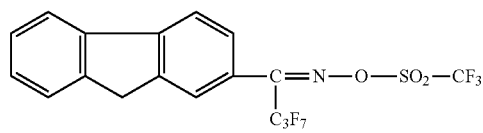
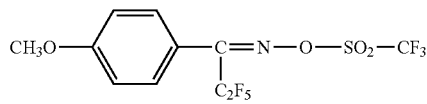
-continued
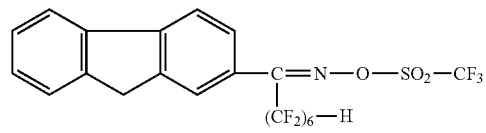
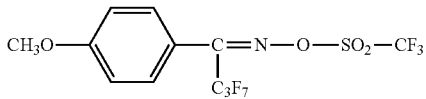
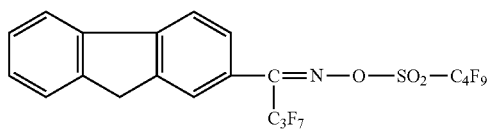
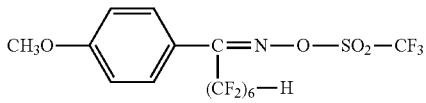

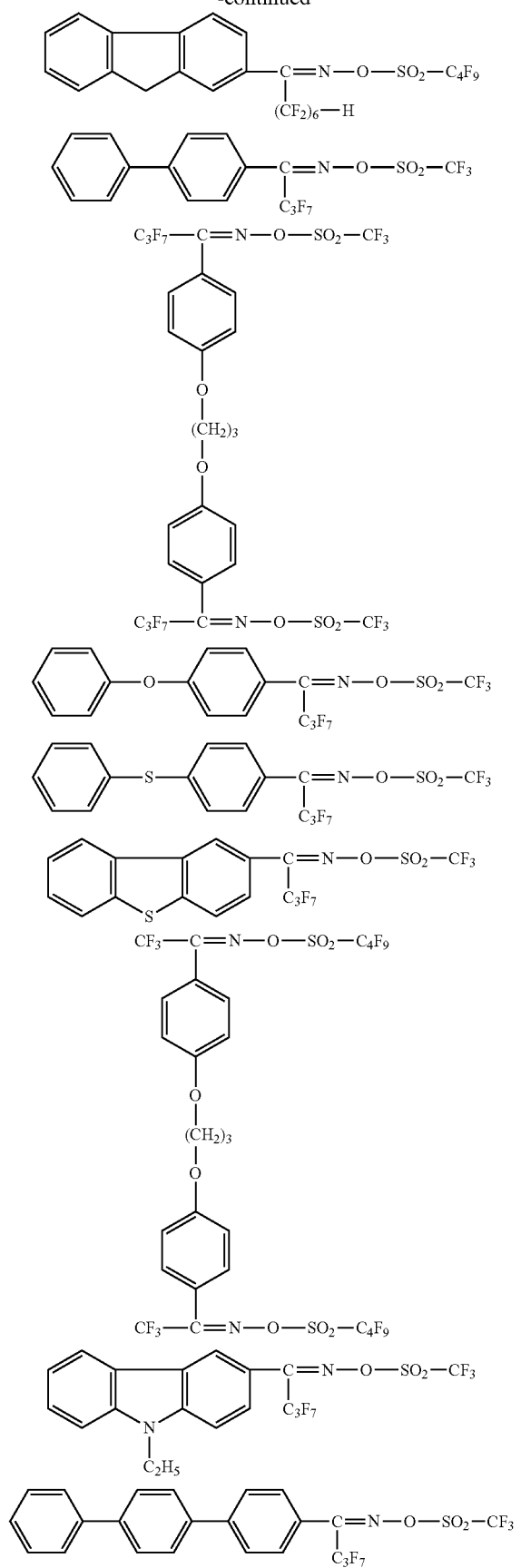
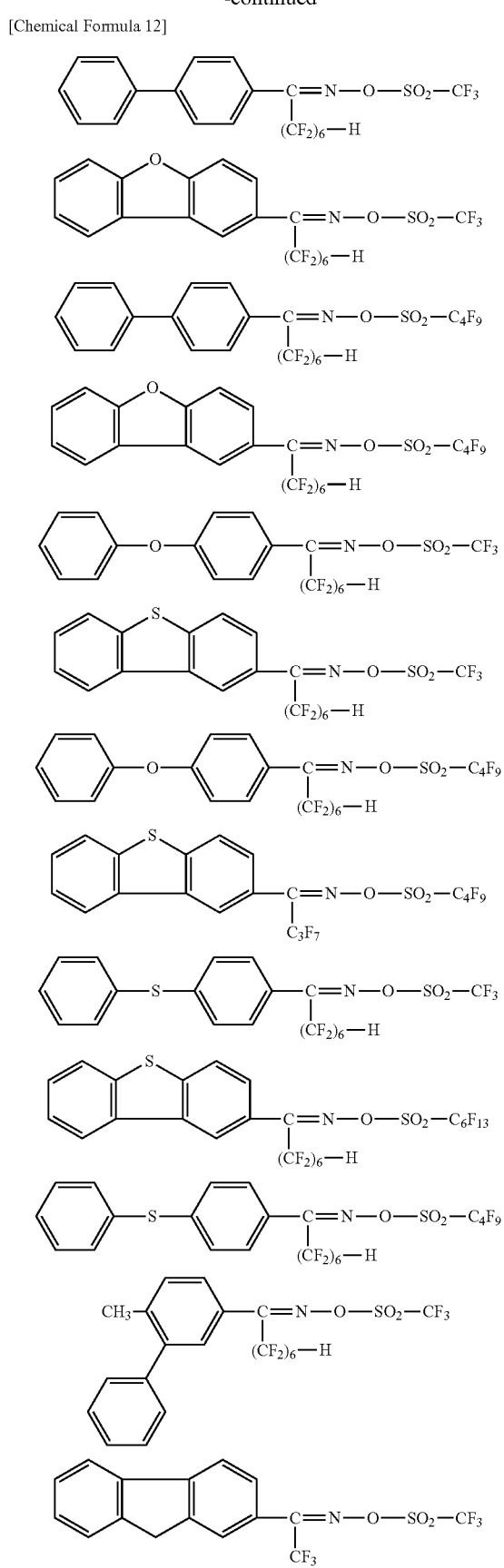

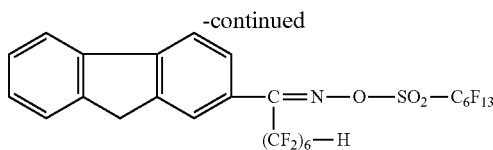

Among the exemplified compounds, the following three compounds are preferred.

[Chemical Formula 13]

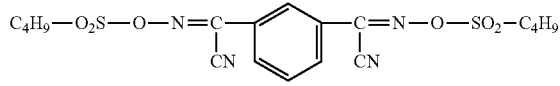

[Chemical Formula 14]

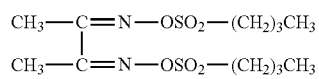

[Chemical Formula 15]

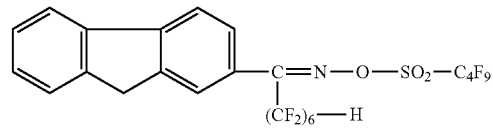

Among the diazomethane-based acid generators, specific examples of bisalkyl or bisarylsulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl) diazomethane.

Furthermore, examples of the poly(bisulfonyl)diazomethanes include 1,3-bis(phenylsulfonyldiazomethylsulfonyl)propane (in the case of A=3), 1,4-bis(phenylsulfonyldiazomethylsulfonyl)butane (in the case of A=4), 1,6-bis(phenylsulfonyldiazomethylsulfonyl)hexane (in the case of A=6), 1,10-bis(phenylsulfonyldiazomethylsulfonyl)decane (in the case of A=10), 1,2-bis(cyclohexylsulfonyldiazomethylsulfonyl)ethane (in the case of B=2), 1,3-bis(cyclohexylsulfonyldiazomethylsulfonyl)propane (in the case of B=3), 1,6-bis(cyclohexylsulfonyldiazomethylsulfonyl)hexane (in the case of B=6), and 1,10-bis(cyclohexylsulfonyldiazomethylsulfonyl)decane (in the case of B=10), which have the following structures.

[Chemical Formula 16]

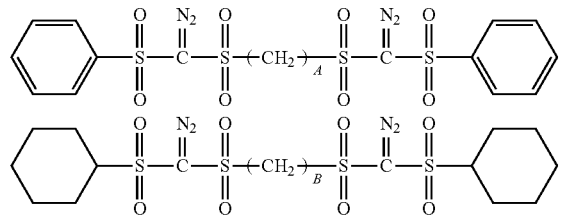

In the present invention, as the component (B), an onium salt having a fluorinated alkylsulfonic acid ion as an anion is preferably used.

As the component (B), the acid generator may be used alone or in a combination of two or more kinds thereof.

The content of the component (B) is 0.5 to 30 parts by mass, and preferably 1 to 10 parts by mass per 100 parts by mass of the component (A). Within the above range, the pattern formation is sufficiently performed. Furthermore, a uniform solution can be obtained, and storage stability is improved, whereby the range is considered preferable.

[Optional Component]

In the positive type resist composition of the present invention, in order to improve the resist pattern shape and the post-exposure stability of the latent image formed by the pattern-wise exposure of the resist layer, a nitrogen-containing organic compound (D) (referred to as the component (D), hereinafter) can also be added as an optional component.

A multitude of these nitrogen-containing organic compounds have already been proposed as the component (D), and any of these known compounds can be optionally used. Examples thereof include mono alkyl amines such as n-hexylamine, n-heptyl amine, n-octyl amine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, tri-n-dodecylamine; and alkyl alcoholamines such as diethanolamine, triethanolamine, diisopropanolamine, triisopropanolamine, di-n-octanolamine, and tri-n-octanolamine. Among these, secondary aliphatic amine or tertiary aliphatic amine are particularly preferable, and trialkylamine having 5 to 10 carbon atoms is more preferable, and tri-n-octyl amine is most preferable.

Theses may be used alone or in a combination of two or more kinds thereof.

The component (D) is used in an amount within a range from usually 0.01 to 5.0 parts by mass per 100 parts by mass of the component (A).

In the positive type resist composition of the present invention, in order to prevent any deterioration in sensitivity caused by the addition of the component (D), and improve the resist pattern shape and the post-exposure stability of the latent image formed by the pattern-wise exposure of the resist layer, an organic carboxylic acid, or a phosphorus oxo acid or derivative thereof (E) (referred to as the component (E), hereinafter) can also be added as another optional component. The component (D) and the component (E) can be used in combination, or either one thereof may also be used alone.

Preferable examples of the organic carboxylic acid include malonic acid, citric acid, malic acid, succinic acid, benzoic acid, and salicylic acid.

Examples of the phosphorus oxo acids or a derivative thereof include phosphoric acid or a derivative thereof such as esters, including phosphoric acid, di-n-butyl phosphate and diphenyl phosphate; phosphonic acid or a derivative thereof such as esters, including phosphonic acid, dimethyl phosphonate, di-n-butyl phosphonate, phenylphosphonic acid, diphenyl phosphonate, and dibenzyl phosphonate; and phosphinic acid or a derivative thereof such as esters, including phosphinic acid and phenylphosphinic acid, and among these, phosphonic acid is particularly preferred.

The component (E) is typically used in an amount within a range from 0.01 to 5.0 parts by mass per 100 parts by mass of the component (A).

Miscible additives can also be added to the positive type resist composition of the present invention according to need, including an additive resin for improving the properties of the resist film, a surfactant for improving the ease of application, a dissolution inhibitor, a plasticizer, a stabilizer, a colorant, a halation prevention agent, and a pigment.

The positive type resist composition of the present invention can be produced by dissolving the component (A) and the component (B), together with various optional components, in an organic solvent.

The organic solvent may be any solvent capable of dissolving various components to generate a uniform solution, and one or more solvents selected from known materials used as the solvents for conventional chemically amplified resists can be suitably selected and used.

Examples of the organic solvent include lactones such as γ-butyrolactone; ketones such as acetone, methyl ethyl ketone, cyclohexanone, methyl isoamyl ketone and 2-heptanone; polyhydric alcohols and derivatives thereof such as ethylene glycol, ethylene glycol monoacetate, diethylene glycol, diethylene glycol monoacetate, propylene glycol, propylene glycol monoacetate, dipropylene glycol, or the monomethyl ether, monoethyl ether, monopropyl ether, monobutyl ether or monophenyl ether of dipropylene glycol monoacetate; cyclic ethers such as dioxane; and esters such as methyl lactate, ethyl lactate (EL), methyl acetate, ethyl acetate, butyl acetate, methyl pyruvate, ethyl pyruvate, methyl methoxypropionate, and ethyl ethoxypropionate.

These organic solvents can be used alone, or as a mixed solvent of two or more kinds thereof.

In particular, a mixed solvent of propylene glycol monomethyl ether acetate (PGMEA) and a polar solvent is preferred. In this case, the mass ratio of PGMEA:the polar solvent is suitably determined based on the compatibility between PGMEA and the polar solvent, but it is preferably within a range from 1:9 to 9:1, and more preferably from 2:8 to 8:2.

Specifically, in the case where EL is added as the polar solvent, the mass ratio of PGMEA:EL is preferably within a range from 1:9 to 9:1, and more preferably from 2:8 to 8:2.

Furthermore, as another organic solvent, a mixed solvent of at least one selected from PGMEA and EL, and γ-butyrolactone, is also preferred. In such cases, the mass ratio of the former and latter components in the mixed solvent is preferably within a range from 70:30 to 95:5.

The amount of the organic solvent used is not particularly limited, but it is suitably selected according to the applied film thickness at any concentration which allows application to a substrate. Generally, the amount of the organic solvent used is in an amount within a range from 2 to 20% by mass, and preferably from 5 to 15% by mass as a solid concentration of the resist composition.

<Method of Forming Resist Pattern>

A method of forming the resist pattern of the present invention is characterized in that it includes the steps of applying the positive type resist composition of the present invention to a substrate to form a resist film; exposing the resist film; and developing the resist film to form a resist pattern. Specifically, the resist pattern can be formed, for example, by the method of forming a resist pattern as described below. Namely, the resist composition is first applied onto the surface of a substrate such as a silicon wafer by using a spinner or the like, and optionally subject to PAB to form a resist film. The formed resist film is selectively exposed by using, for example, an ArF exposure device, an electron beam irradiation device, and an EUV exposure device, through a mask pattern, or directly irradiating an electron beam without a mask pattern, and then PEB (Post Exposure Bakeing) is conducted. Subsequently, developing is conducted using an alkali developing solution, and rinsing is conducted, thereby washing the developer on the substrate and the resist composition dissolved by the developer and drying to obtain a resist pattern.

This process can be performed using a well-known means. It is preferable that the operation conditions, etc. be suitably selected according to the composition and characteristics of the positive type resist composition used.

The exposure source is not particularly limited, but radiations such as an ArF excimer laser, a KrF excimer laser, an $F_2$ excimer laser, an EUV (extreme ultraviolet), a VUV (vacuum ultraviolet), an electron beam, an X-ray, and a soft X-ray can be used. Particularly, the positive type resist composition according to the present invention is effective for the ArF excimer laser, the electron beam or EUV, and particularly the ArF excimer laser or the electron beam.

Furthermore, in some cases, a post-bake process can be conducted after the alkali developing, and an organic or inorganic anti-reflective film can be provided between the substrate and the resist film.

As described above, by using the compound (A1) of the present invention, a high resolution resist pattern can be formed, and roughness can be reduced.

Moreover, in the present invention, as described above, considering that since the compound (A1) has uniform properties, a resist film having uniform properties (alkali, hydrophilic and hydrophobic properties, or the like) can be formed and defects can be reduced. As used herein, defects indicate problems in general, for example, detected by a surface defect inspection apparatus (trade name: "KLA") manufactured by KLA-Tencor Corp. when the resist pattern after developing is observed from directly above. Examples of the problems include scum after developing, bubbles, dust, bridges between resist patterns, color blurring, and precipitates.

Furthermore, considering that since the compound (A1) has uniform properties, the solubility in an organic solvent, etc. is also uniform and the storage stability of the positive type resist composition comprising the compound (A1) is also improved.

EXAMPLES

The present invention will now be illustrated in more detail with reference to the following examples, but these examples should not be construed as limiting the scope of the invention in any way.

Synthesis Example 1

Synthesis of Compound (2) (Cholic Acid Derivative)

6 g of cholic acid (1) was dissolved in 50 g of tetrahydrofuran, and 3.04 g of triethylamine was added thereto. The mixture was stirred for 10 minutes, and 1.17 g of 1,2-bis (chloromethoxy)ethane was added thereto. The mixture was stirred at room temperature for 10 hours. After completion of the reaction, the mixture was extracted from water/ethyl acetate, and the ethyl acetate solution was dried over sodium sulfate, and concentrated under reduced pressure to obtain 3.5 g of a compound (2).

Furthermore, in the following Synthesis Examples, "Me" means a methyl group, and "Et" means an ethyl group in the chemical formulae.

[Chemical Formula 17]

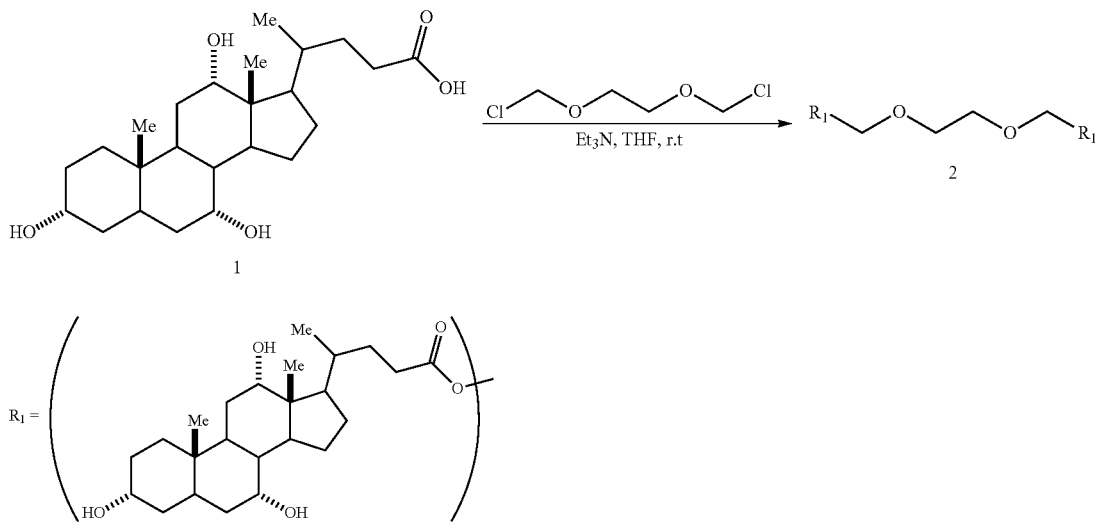

Identification of (2)

$^1$H-NMR (deuterated DMSO, internal standard: tetramethylsilane): δ 5.21 s 4H, 4.26-4.31 m 2H, 4.07-4.11 m 2H, 3.96-3.99 m 2H, 3.74-3.81 m 2H, 3.71 s 4H, 3.57-3.64 m 2H, 3.13-3.24 m 2H, 2.31-2.72 m 2H, 2.06-2.31 m 6H, 1.93-2.04 m 2H, 1.58-1.85 m 12H, 1.11-1.51 m 22H, 0.78-1.03 m 16H, 0.60 s 6H IR (cm$^{-1}$): 3410, 2937, 2869, 1740

Furthermore, Tg (glass transition temperature) was 177° C. In the present Synthesis Example, Tg was measured using a thermal analysis instrument TG/DTA6200 (manufactured by Seiko Instrument Inc.) under the condition of a heating rate of 10° C./min.

Synthesis Example 2

Synthesis of Compound (3) (Cholic Acid Derivative)

5 g of cholic acid (1) was dissolved in 50 g of tetrahydrofuran, and 3.04 g of triethylamine was added thereto. The mixture was stirred for 10 minutes, and 1.06 g of 1,3-bis(chloromethoxy)propane was added thereto. The mixture was stirred at room temperature for 10 hours. After completion of the reaction, the mixture was extracted from water/ethyl acetate, and the ethyl acetate solution was dried over sodium sulfate, and concentrated under reduced pressure to obtain 3.0 g of a compound (3).

[Chemical Formula 18]

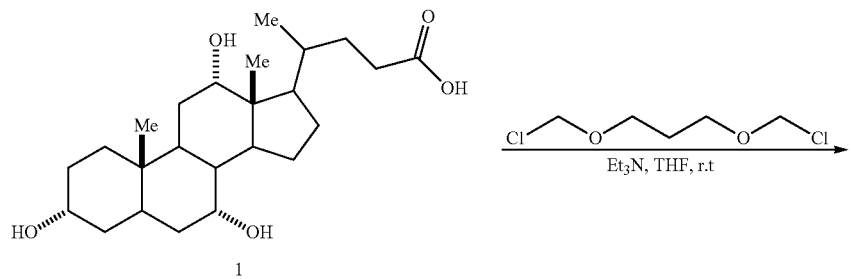

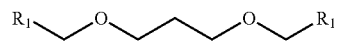

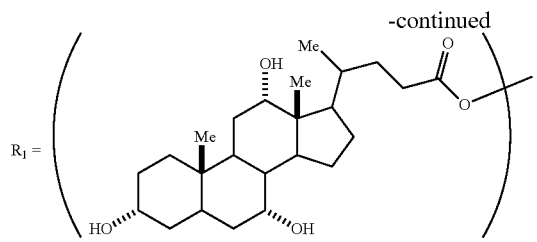

Identification of (3)

$^1$H-NMR (deuterated DMSO, internal standard: tetramethylsilane): δ 5.20 s 4H, 4.26-4.30 m 2H, 4.07-4.10 m 2H, 3.93-3.98 m 2H, 3.75-3.81 m 2H, 3.57-3.65 m 6H, 3.13-3.24 m 2H, 2.30-2.41 m 2H, 2.09-2.30 m 6H, 1.93-2.05 m 2H, 1.58-1.86 m 14H, 1.11-1.50 m 22H, 0.76-1.03 m 16H, 0.58 s 6H IR (cm$^{-1}$): 3401, 2937, 2869, 1740

Furthermore, Tg was 177° C.

Synthesis Example 3

Synthesis of Compound (4) (Cholic Acid Derivative)

8 g of cholic acid (1) was dissolved in 60 g of tetrahydrofuran, and 3.04 g of triethylamine was added thereto. The mixture was stirred for 10 minutes, and 2.36 g of 1,4-bis(chloromethoxy)cyclohexane was added thereto. The mixture was stirred at room temperature for 10 hours. After completion of the reaction, the mixture was extracted from water/ethyl acetate, and the ethyl acetate solution was dried over sodium sulfate, and concentrated under reduced pressure to obtain 5.0 g of a compound (4).

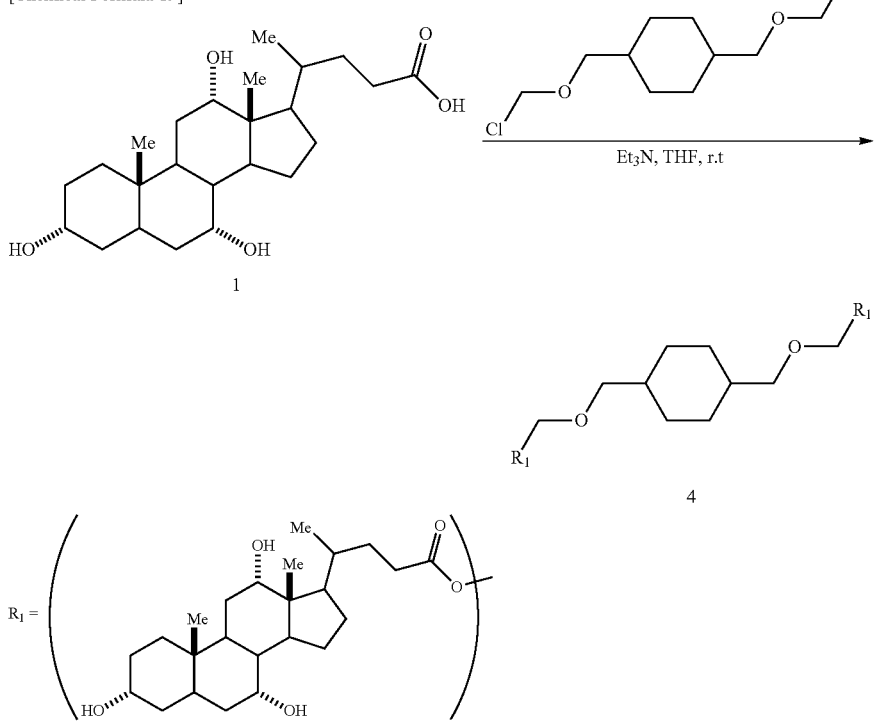

[Chemical Formula 19]

Identification of (4)

$^1$H-NMR (deuterated DMSO, internal standard: tetramethylsilane): δ 5.19 s 4H, 4.27-4.29 m 2H, 4.08-4.10 m 2H, 3.96-3.98 m 2H, 3.76-3.80 m 2H, 3.59-3.63 m 2H, 3.36-3.40 m 4H, 3.13-3.23 m 2H, 2.29-2.40 m 2H, 2.10-2.29 m 6H, 1.92-2.06 m 2H, 1.58-1.87 m 14H, 1.07-1.52 m 30H, 0.77-1.03 m 16H, 0.58 s 6H IR (cm$^{-1}$): 3413, 2934, 2867, 1740

Furthermore, Tg was 100° C.

Synthesis Example 4

Synthesis of Compound (6) (Lithocholic Acid Derivative)

6 g of lithocholic acid (5) was dissolved in 50 g of tetrahydrofuran, and 3.04 g of triethylamine was added thereto. The mixture was stirred for 10 minutes, and 1.27 g of 1,2-bis(chloromethoxy)ethane was added thereto. The mixture was stirred at room temperature for 10 hours. After completion of the reaction, the mixture was extracted from water/ethyl acetate, and the ethyl acetate solution was dried over sodium sulfate, and concentrated under reduced pressure to obtain 6.5 g of a compound (6).

Synthesis Example 5 Compound (7) (Lithocholic Acid Derivative)

5 g of lithocholic acid (5) was dissolved in 50 g of tetrahydrofuran, and 3.04 g of triethylamine was added thereto. The

[Chemical Formula 20]

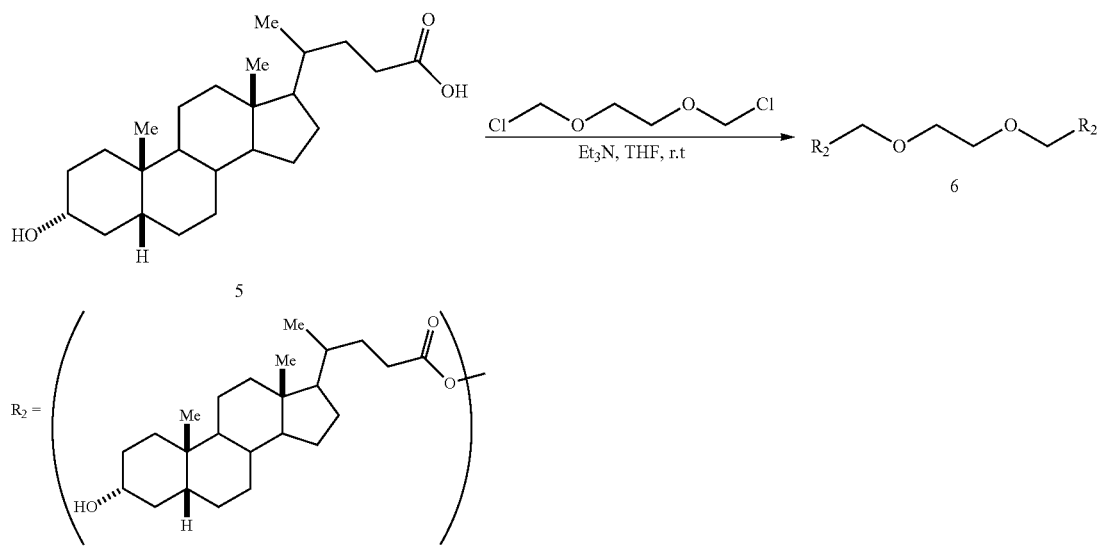

Identification of (6)

$^1$H-NMR (deuterated DMSO, internal standard: tetramethylsilane): δ 5.21 s 4H, 4.36-4.47 m 2H, 3.69 s 4H, 3.24-3.42 m 2H, 2.30-2.41 m 2H, 2.18-2.23 m 2H, 1.88-1.95 m 2H, 1.45-1.86 m 14H, 0.95-1.43 m 32H, 0.84-0.95 m 16H, 0.61 s 6H IR (cm$^{-1}$): 3400, 2935, 2865, 1743

Furthermore, Tg was 151° C.

mixture was stirred for 10 minutes, and 1.15 g of 1,3-bis(chloromethoxy)propane was added thereto. The mixture was stirred at room temperature for 10 hours. After completion of the reaction, the mixture was extracted from water/ethyl acetate, and the ethyl acetate solution was dried over sodium sulfate, and concentrated under reduced pressure to obtain 4.3 g of a compound (7).

[Chemical Formula 21]

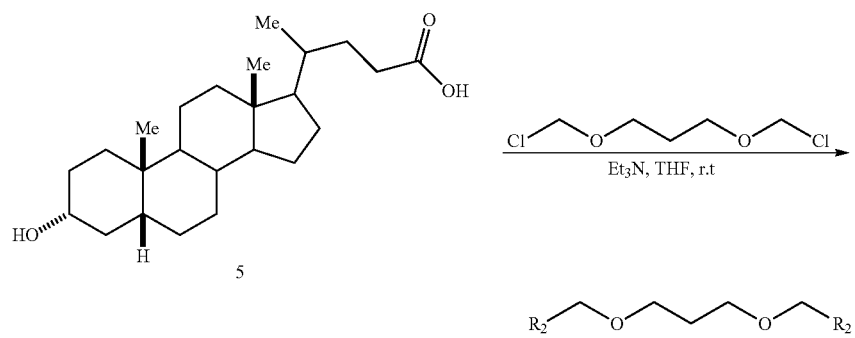

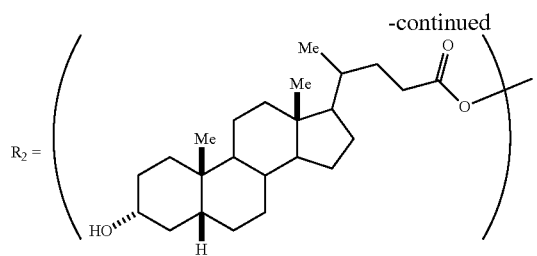

Identification of (7)

$^1$H-NMR (deuterated DMSO, internal standard: tetramethylsilane): δ 5.20 s 4H, 4.33-4.53 m 2H, 3.56-3.63 m 4H, 3.18-3.42 m 2H, 2.29-2.40 m 2H, 2.17-2.29 m 2H, 1.88-1.96 m 2H, 1.44-1.88 m 16H, 0.95-1.44 m 32H, 0.80-0.95 m 16H, 0.60 s 6H IR (cm$^{-1}$): 3392, 2936, 2865, 1743
Furthermore, Tg was 160° C.

Synthesis Example 6

Synthesis of Compound (8) (Lithocholic Acid Derivative)

8 g of lithocholic acid (5) was dissolved in 60 g of tetrahydrofuran, and 3.04 g of triethylamine was added thereto. The mixture was stirred for 10 minutes, and 2.56 g of 1,4-bis(chloromethoxy)cyclohexane was added thereto. The mixture was stirred at room temperature for 10 hours. After completion of the reaction, the mixture was extracted from water/ethyl acetate, and the ethyl acetate solution was dried over sodium sulfate, and concentrated under reduced pressure to obtain 8.2 g of a compound (8).

[Chemical Formula 22]

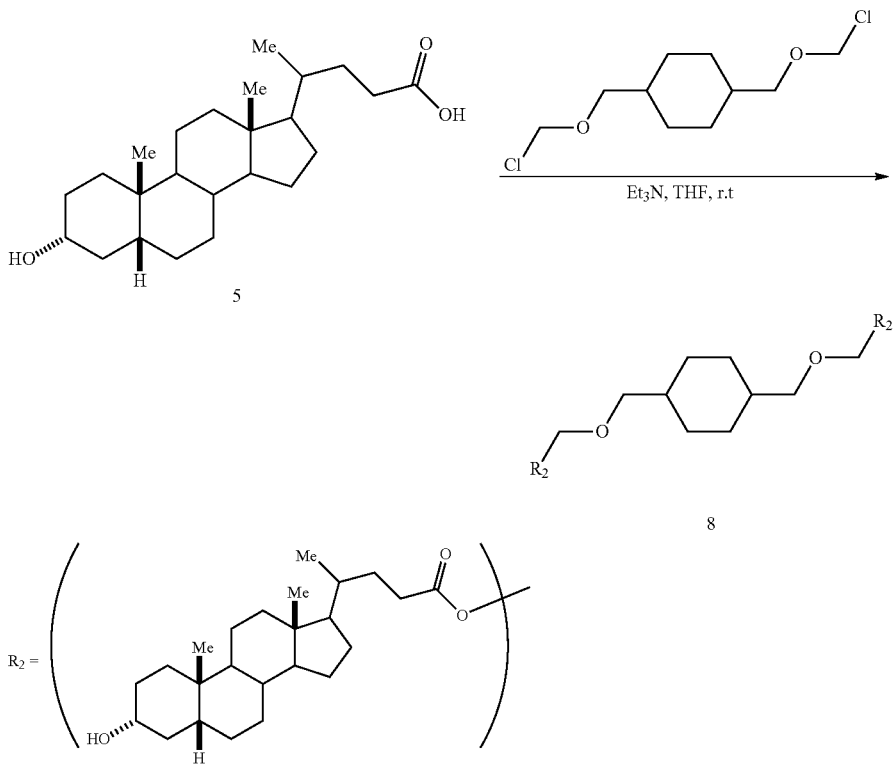

Identification of (8)

$^1$H-NMR (deuterated DMSO, internal standard: tetramethylsilane): δ 5.19 s 4H, 4.33-4.49 m 2H, 3.18-3.43 m 6H, 2.28-2.39 m 2H, 2.16-2.28 m 2H, 1.88-1.96 m 2H, 0.97-1.88 m 56H, 0.80-0.96 m 16H, 0.60 s 6H IR (cm$^{-1}$): 3400, 2935, 2865, 1743
Furthermore, Tg was 144° C.

<Solubility in Organic Solvent>

100 parts by mass of each of the compounds (2) to (4), and the compounds (6) to (8) as synthesized in Synthesis Examples 1 to 6 was added to 1570 parts by mass of propylene glycol monomethyl ether acetate, and the mixture was stirred. As a result of observation with the naked eye, there was no undissolved remnant, indicating that the solubility in the organic solvent was good.

<Applicability>

100 parts by mass of each of the compounds (2) to (4), and the compounds (6) to (8) as synthesized in Synthesis Examples 1 to 6 was added to 1570 parts by mass of an organic solvent of propylene glycol monomethyl ether acetate, and ultrasonic treatment (dissolution treatment) was performed for dissolution using an ultrasonic cleaner. The solution was spin-coated on a wafer at 1500 rpm, and optionally subject to PAB at 110° C. for 90 seconds, and then it was determined whether an amorphous film was formed, by observing with the naked eye whether it was transparent.

Further, a film that is not transparent is not an amorphous film. As a result, it was confirmed that an amorphous resist film can be formed.

<Measurement of Absorbance>

The compounds (3) and (4) were measured for absorbance of light at 193 nm wavelength. The measurement device was VUV-200 Vacuum Ultraviolet Spectrophotometer (manufactured by Japan Spectroscopic Co., Ltd.). The measurement conditions are shown below.

(1) Without a substrate, the absorbance is measured (as background).

(2) The absorbance of a magnesium fluoride substrate is measured.

(3) A solution of 100 parts by mass of the target to be dissolved in 1570 parts by mass of PGMEA is spin-coated on a magnesium fluoride substrate to form a film having a thickness of 150 nm, and then the absorbance is measured.

(4) (Value obtained in (3)−Value obtained in (2))=Absorbance of Film

As a result, the absorbances per 1 μm were 0.33 (Compound (3)), and 0.27 (Compound (4)), respectively.

<Dissolution Contrast (ArF Exposure Residual Film Curve)>

100 parts by mass of the compounds (2) to (4), and (6) to (8) as synthesized above, as the component (A), and any one of the acrylic terpolymers for comparison, 3 parts by mass of triphenylsulfonium nonafluorobutanesulfonate, and 0.3 part by mass of triethanol amine, were dissolved in 1100 parts by mass of propylene glycol monomethyl ether acetate to prepare a positive type resist composition.

The positive type resist composition was uniformly applied onto an 8-inch silicon wafer by using a spinner, and subject to PAB at 110° C. for 90 seconds to form a resist film.

The resist film was exposed using an ArF excimer laser, and then subject to PEB at 110° C. for 90 seconds. Subsequent developing was conducted for 60 seconds in an aqueous solution of tetramethylammonium hydroxide (TMAH) with a concentration of 0.5% by mass. At that time, the change in the residual film rates (the film thickness after developing/the film thickness upon formation of a film (before exposure)) by the change in the exposure amounts of the ArF excimer laser, was determined to obtain a curve for a residual film.

The acrylic terpolymers for comparison is 2-methyl-2-adamantylmethacrylate/α-methacryloyloxy γ-butyrolactone/3-hydroxy-1-adamantylmethacrylate (molar ratio 4/4/2, molecular weight 10000, distribution 2.0) copolymer.

The results are shown in FIG. 1. From these results, it was confirmed that the compounds (2) to (4), and (6) to (8) of the present invention increase the alkali solubility under the action of an acid, and thus, serve as the base component or the dissolution inhibitor in the positive type resist composition.

Furthermore, it was confirmed that the positive type resist compositions including the compounds (2) to (4), and (6) to (8) of the present invention have a contrast of no less than the positive type resist composition comprising the acrylic terpolymers for comparison.

Examples 1 to 4

All of the components were mixed and dissolved at the compositions and blending amounts as shown in Table 1 to prepare a positive type resist composition solution. Furthermore, the unit of the blending amount as shown in Table 1 is a parts by mass. 100 parts by mass of the component (A) was used. Furthermore, the abbreviations in Table 1 have the following meanings.

TPS-PFBS: Triphenylsulfonium nonafluorobutanesulfonate
Amine 1: Tri-n-octyl amine
Amine 2: Triethanol amine
PGMEA: Propylene glycol monomethyl ether acetate

TABLE 1

|  | Component (A) | Component (B) | Blending amount | Component (D) | Blending amount | Organic solvent | Blending amount |
|---|---|---|---|---|---|---|---|
| Example 1 | Compound (2) | TPS-PFBS | 10 | Amine 1 | 1 | PGMEA | 1370 |
| Example 2 | Compound (3) | TPS-PFBS | 10 | Amine 1 | 1 | PGMEA | 1370 |
| Example 3 | Compound (4) | TPS-PFBS | 3 | Amine 2 | 0.3 | PGMEA | 1100 |
| Example 4 | Compound (4) | TPS-PFBS | 10 | Amine 1 | 1 | PGMEA | 1370 |

The obtained positive type resist composition solution was used for the following evaluation. The results are shown in Table 2.

<Sensitivity (Electron Beam (EB))>

The positive type resist composition solutions of Examples 1, 2, and 4 were uniformly applied onto an 8-inch silicon wafer which had been treated with hexamethyldisilazane by using a spinner, and subject to PAB at 110° C. for 90 seconds to form a resist film (film thickness: 150 nm).

The resist film was exposed using an electron beam drawing device HL-800D (VSB) (manufactured by HITACH, Ltd.)) at an accelerated voltage of 70 kV, subject to PEB at 110° C. for 90 seconds, subject to developing using an aqueous solution of tetramethylammonium hydroxide (TMAH) at a concentration of 2.38% by mass (23° C.) for 60 seconds, and then rinsed with pure water for 30 sec to form a line-andspace (L/S) pattern. Then, the exposure amount Eop (μC/cm²) for obtaining 200 nm of L/S pattern at 1:1 was determined.

<Sensitivity (ArF Excimer Laser)>

The material for an organic anti-reflective film (ARC-29 manufactured by Brewer Science, Inc.) was applied onto an 8-inch silicon wafer, and sintered at 225° C. for 60 sec to form an anti-reflective film having a film thickness of 77 nm, which was used as a substrate.

The positive type resist composition of Example 3 was uniformly applied onto the substrate by using a spinner, and subject to PAB at 110° C. for 90 seconds to form a resist film (film thickness: 150 nm).

The resist film was selectively exposed using an ArF exposure device (wavelength: 193 nm) NSR-S302 (manufactured by Nikon Corp., NA (numerical aperture)=0.60, ⅔ annular illumination) through a 6% halftone mask, subject to PEB at 110° C. for 90 seconds, subject to developing using an aqueous solution of TMAH at a concentration of 2.38% by mass (23° C.) for 60 seconds, and then rinsed with pure water for 30 sec to form an L/S pattern. Then, the exposure amount Eop (μC/cm²) for obtaining 200 nm of L/S pattern at 1:1 was determined.

<Resolution>

The limit resolution (nm) for the above-described Eop was determined using a scanning electron microscope S-9220 (manufactured by Hitachi, Ltd.).

TABLE 2

|  | Component (A) | Light source | Eop | Limit resolution |
|---|---|---|---|---|
| Example 1 | Compound (2) | EB | 18 μC/cm² | 130 nm |
| Example 2 | Compound (3) | EB | 10 μC/cm² | 150 nm |
| Example 3 | Compound (4) | ArF | 29 mJ/cm² | 130 nm |
| Example 4 | Compound (4) | EB | 18 μC/cm² | 120 nm |

From the above results, the positive type resist composition including the compound of the present invention had good sensitivity and allowed the formation of a high resolution resist pattern even with any one of EB and ArF excimer lasers.

<Evaluation of Etching Resistance>

0.5 g of each of the compounds (2), (4), and (8), and the acrylic terpolymers which had been used for evaluation of the "dissolution contrast" as above was dissolved in 2 g of PGMEA to prepare a resin solution. The obtained resin solution was uniformly applied to an 8-inch silicon wafer by using a spinner, and subject to PAB at 110° C. for 90 seconds, to form a resist film (film thickness: 150 nm). Thereafter, etching was performed using an RIE (Reactive ion etching) device RIE-10 NR (trade name, manufactured by Samco Inc.). The film thickness of the resist film after etching was measured, and from the values, the reduced film thickness (Å) (=difference between the film thickness before and that after etching), and the etch rate (=Reduced film thickness (Å)/Etching time (seconds (s))) was determined to evaluate the etching resistance. The results are shown in Table 3.

TABLE 3

|  | Reduced film thickness | Etch rate (Å/s) |
|---|---|---|
| Compound (2) | 255 | 8.5 |
| Compound (4) | 188 | 6.3 |
| Compound (8) | 193 | 6.4 |
| Acryl | 448 | 14.9 |

Evaluation Conditions:

Gas: $CF_4/CHF_3/Ar=23/20/150$ (sccm)

Pressure in chamber: 40 Pa

Output power (Power) applied for generation of plasma: 300 W

Treatment time: 30 seconds

<Evaluation of Surface Roughness>

The following (a) to (c) positive type resist compositions were uniformly applied onto an 8-inch silicon wafer which had been treated with hexamethyldisilazane by using a spinner, and subject to PAB at 110° C. for 90 seconds to form a resist film (film thickness: 150 nm).

(a) The positive type resist composition of Example 1.

(b) The positive type resist composition of Example 3.

(c) The same positive type resist composition as in Example 1, except that the compound (2) was changed to a resin which has 37.4% of the hydroxyl groups of polyhydroxy styrene protected, and has a mass-average molecular weight of 8000, and a distribution of 2.65, and the organic solvent was changed to a mixed solvent of PGMEA and EL (mass ratio: 6:4).

The obtained resist film was exposed using an electron beam drawing device HL-800D (VSB) (manufactured by HITACH, Ltd) at an accelerated voltage of 70 kV, subject to exposure at an exposure amount Eop (μC/cm²) to make the film thickness after developing be 50% of the initial film thickness, subject to post exposure bake (PEB) at 110° C. for 90 seconds, subject to developing using an aqueous solution of TMAH at a concentration of 2.38% by mass (23° C.) for 60 seconds, and then rinsed with pure water for 30 seconds.

After rinsing, the surface of the resist film was observed using an AFM (atomic force microscope: manufactured by Veeco Instrument Inc., di NanoScope IV/D5000), and then a root mean square (Rms) surface roughness (nm) was determined therefrom.

As a result, the surface roughness of (a) was 0.7 nm, the surface roughness of (b) was 2.1 nm; and the surface roughness of (c) was 22.9 nm.

Synthesis Example 7

Synthesis of Low-Molecular-Weight Compound (10)

3 g of the compound (9) was dissolved in 25 g of tetrahydrofuran (THF), and 1 g of triethylamine was added thereto. The mixture was stirred at room temperature for 10 minutes, and 0.59 g of 1,2-bis(chloromethoxy)ethane was added dropwise thereto. The mixture was stirred at room temperature for 10 hours. After completion of the reaction, the reaction solution was filtered, and concentrated. The concentrated solution was extracted from water/ethyl acetate (mass ratio: 1:1), and the ethyl acetate phase was concentrated under reduced pressure to obtain 2.5 g of a compound (10).

[Chemical Formula 23]

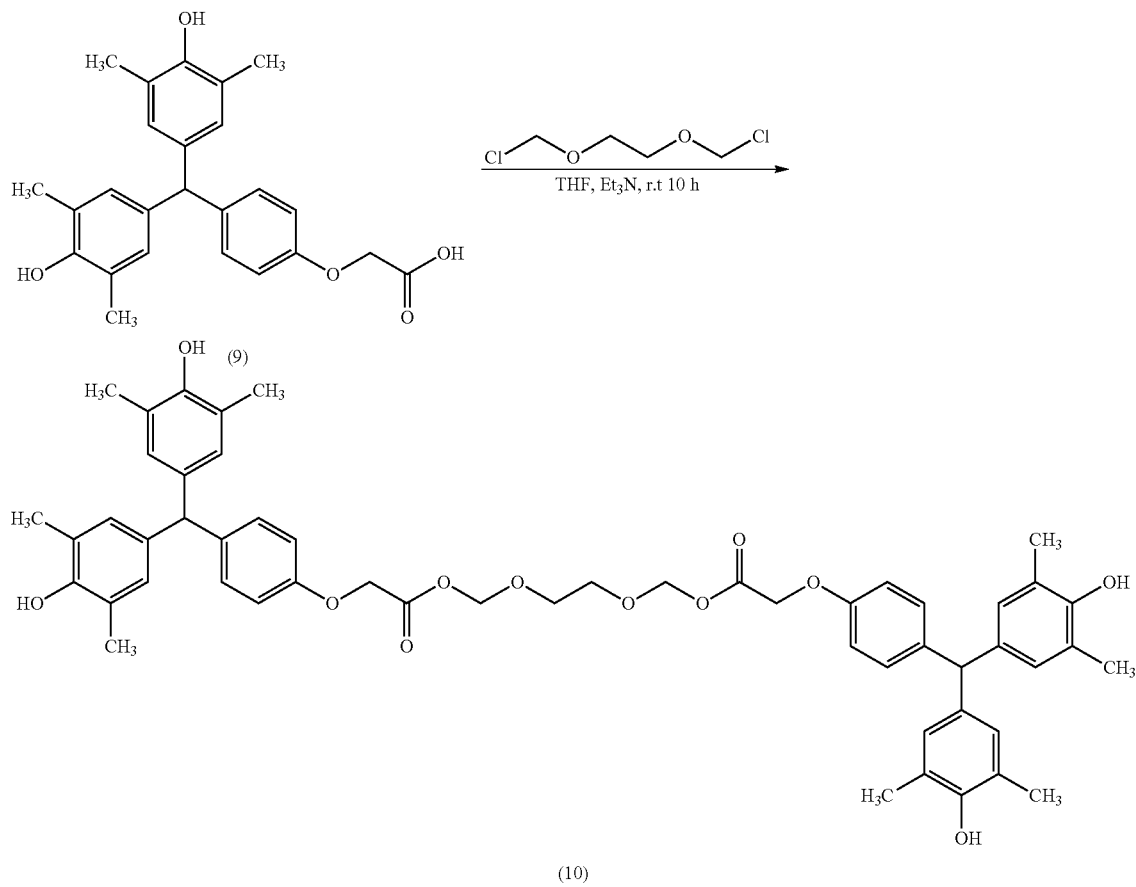

The compound (10) was analyzed by $^1$H-NMR and IR.

$^1$H-NMR (deuterated dimethylsulfoxide (DMSO), internal standard: tetramethylsilane, 400 MHz): δ (ppm)=7.98 brs 4H(H$^a$), 6.96 d 4H(H$^b$) J$_{bc}$=8.4 Hz, 6.81 d 4H(H$^c$) J$_{cb}$=8.4 Hz, 6.59 s 8H(H$^d$), 5.32 s 4H(H$^e$), 5.15 s 2H(H$^f$), 4.77 s 4H(H$^g$), 3.67 s 4H(H$^h$), 2.08 s 24H(H$^i$).

IR: 3472, 2920, 2877, 1758, 1604, 1509 (cm$^{-1}$)

From the results, it was confirmed that the compound (10) has the following structure.

[Chemical Formula 24]

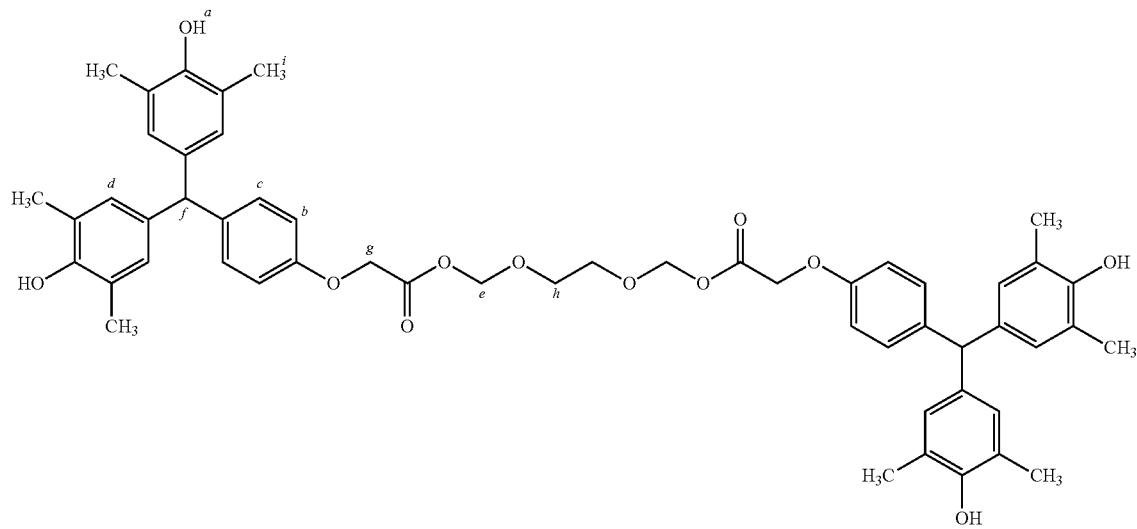

Synthesis Example 8

Synthesis of Low-Molecular-Weight Compound (11)

3 g of the compound (9) was dissolved in 25 g of THF, and 1 g of triethylamine was added thereto. The mixture was stirred at room temperature for 10 minutes, and 0.64 g of 1,3-bis(chloromethoxy)propane was added dropwise thereto. The mixture was stirred at room temperature for 10 hours. After completion of the reaction, the reaction solution was filtered, and concentrated. The concentrated solution was extracted from water/ethyl acetate (mass ratio: 1:1), and the ethyl acetate phase was concentrated under reduced pressure to obtain 2.4 g of a compound (11).

The compound (11) was analyzed by $^1$H-NMR and IR.

$^1$H-NMR (deuterated dimethylsulfoxide (DMSO), internal standard: tetramethylsilane, 400 MHz): δ (ppm)=7.98 s 4H(H$^a$), 6.95 d 4H(H$^b$) J$_{bc}$=8.4 Hz, 6.81 d 4H(H$^c$) J$_{cb}$=8.4 Hz, 6.59 s 8H(H$^d$), 5.28 s 4H(H$^e$), 5.14 s 2H(H$^f$), 4.75 s 4H(H$^g$), 3.58 t 4H(H$^h$) J$_{hj}$=6.2 Hz, 2.09 s 24H(H$^i$), 1.60 quin 2H(H$^j$) J$_{jh}$=6.2 Hz IR: 3477, 2950, 1755, 1607, 1509 (cm$^{-1}$)

[Chemical Formula 25]

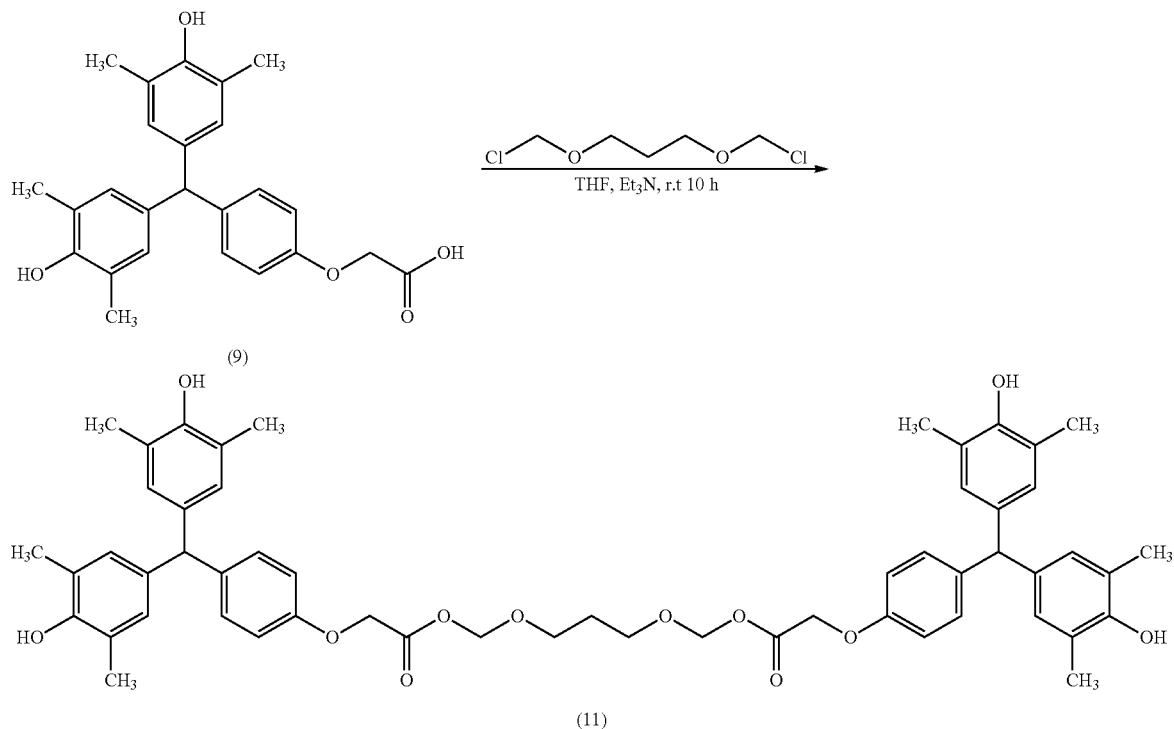

From the results, it was confirmed that the compound (11) has the following structure.

[Chemical Formula 26]

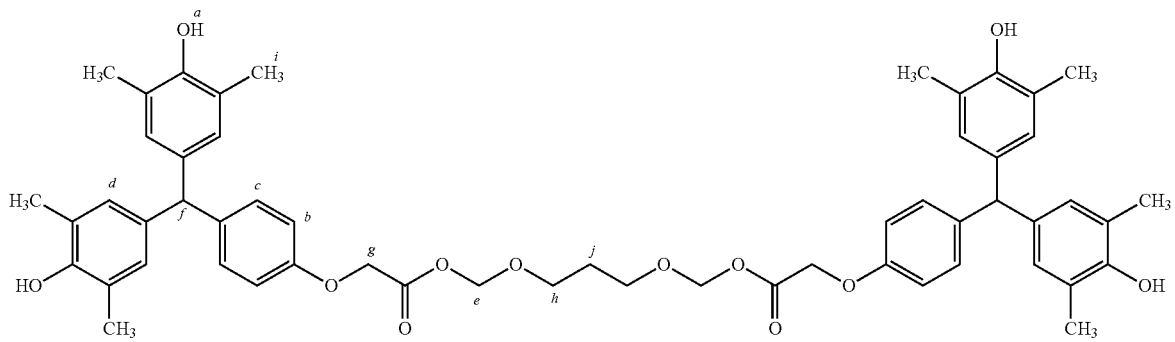

Synthesis Example 9

Synthesis of Low-Molecular-Weight Compound (12)

3 g of the compound (9) was dissolved in 25 g of THF, and 1 g of triethylamine was added thereto. The mixture was stirred at room temperature for 10 minutes, and 0.89 g of 1,4-bis(chloromethoxymethyl)cyclohexane was added dropwise thereto. The mixture was stirred at room temperature for 10 hours. After completion of the reaction, the reaction solution was filtered, and concentrated. The concentrated solution was extracted from water/ethyl acetate (mass ratio: 1:1), and the ethyl acetate phase was concentrated under reduced pressure to obtain 2.5 g of a compound (12).

[Chemical Formula 27]

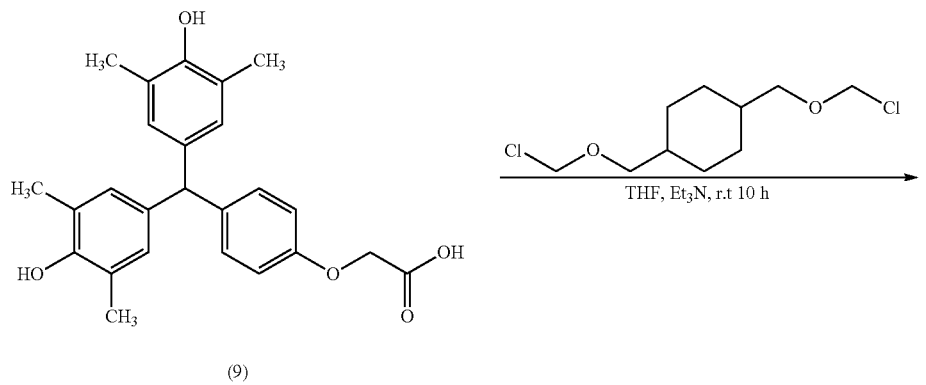

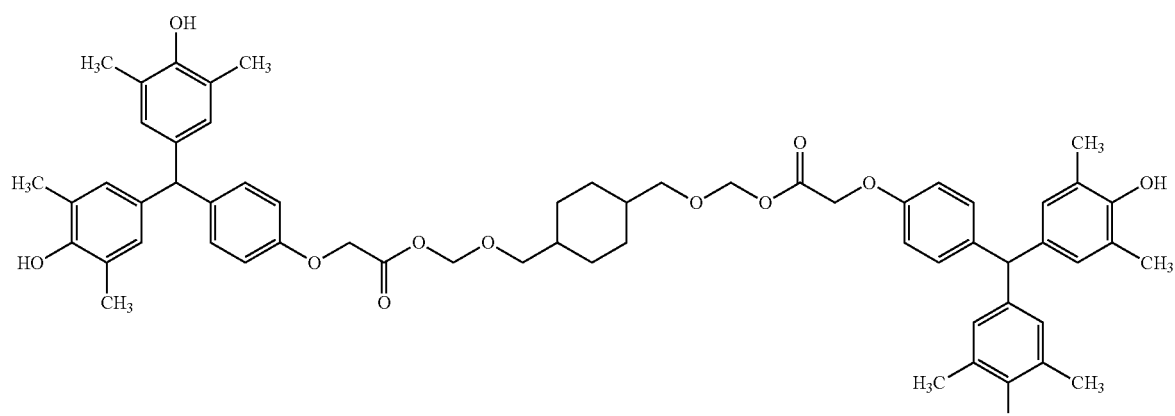

(12)

The compound (12) was analyzed by $^1$H-NMR and IR.

$^1$H-NMR (deuterated dimethylsulfoxide (DMSO), internal standard: tetramethylsilane, 400 MHz): δ (ppm)=7.99 s 4H(H$^a$), 6.96 d 4H(H$^b$) J$_{bc}$=8.4 Hz, 6.80 d 4H(H$^c$) J$_{cb}$=8.4 Hz, 6.58 s 8H(H$^d$), 5.30 s 4H(H$^e$), 5.15 s 2H(H$^f$), 4.76 s 4H(H$^g$), 3.26~3.46 m 4H(H$^h$), 2.06 s 24H(H$^i$), 0.78~1.71 m 10H(H$^j$)

IR: 3476, 2922, 2873, 1756, 1607, 1509 (cm$^{-1}$)

From the results, it was confirmed that the compound (12) has the following structure.

[Chemical Formula 28]

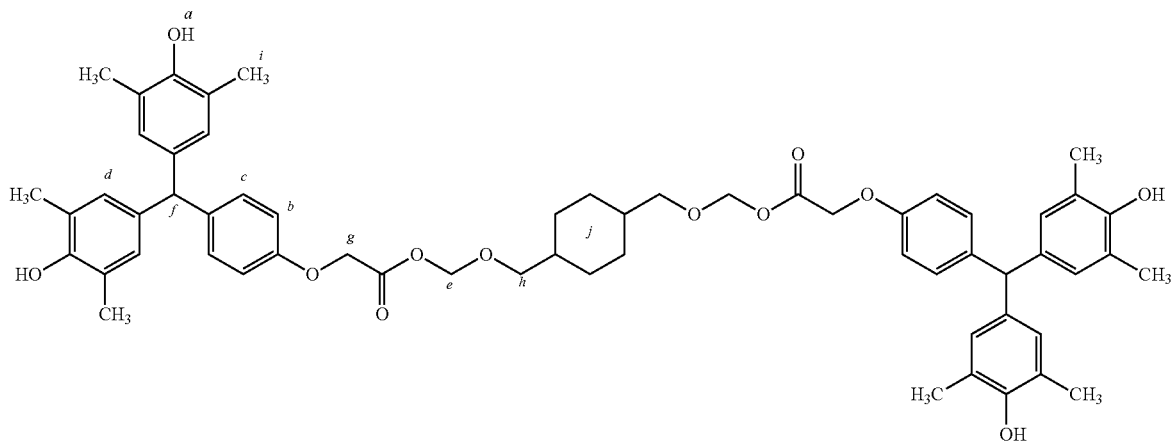

Synthesis Example 10

Synthesis of Low-Molecular-Weight Compound (13)

10 g of the compound (11) was dissolved in 75 g of tetrahydrofuran, and 3.04 g of triethylamine was added thereto. The mixture was stirred at room temperature for 10 minutes, and 2.97 g of 1,4-bis(chloromethoxymethyl)cyclohexane was added dropwise thereto. The mixture was stirred at room temperature for 10 hours. After completion of the reaction, the reaction solution was filtered, and concentrated. The concentrated solution was extracted from water/ethyl acetate (mass ratio: 1:1), and the ethyl acetate phase was concentrated under reduced pressure to obtain 2.5 g of a compound (13).

[Chemical Formula 29]

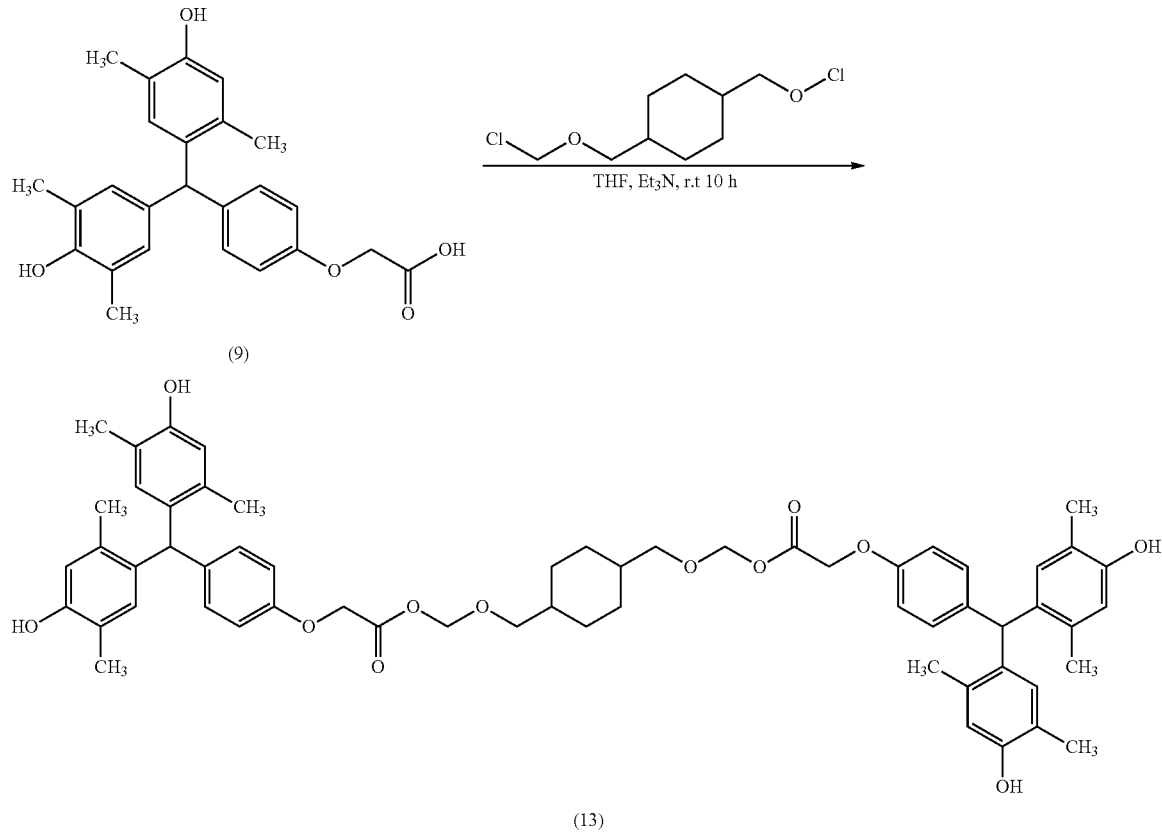

The compound (13) was analyzed by $^1$H-NMR and IR.

$^1$H-NMR (deuterated dimethylsulfoxide (DMSO), internal standard: tetramethylsilane, 400 MHz): δ (ppm)=8.92 s 4H(H$^a$), 6.87 d 4H(H$^b$) J$_{bc}$=8.4 Hz, 6.80 d 4H(H$^c$) J$_{cb}$=8.4 Hz, 6.56 s 4H(H$^d$), 6.31 s 4H(H$^e$), 5.35 s 2H(H$^f$), 5.29 s 4H(H$^g$), 4.75 s 4H(H$^h$), 3.15~3.54 m 4H(H$^i$), 1.99 s 12H(H$^j$), 1.94 s 12H(H$^k$), 0.77~1.74 m 10H(H$^l$)

IR: 3365, 2924, 2852, 1748, 1609, 1587, 1509 (cm$^{-1}$)

From the results, it was confirmed that the compound (13) has the following structure.

[Chemical Formula 30]

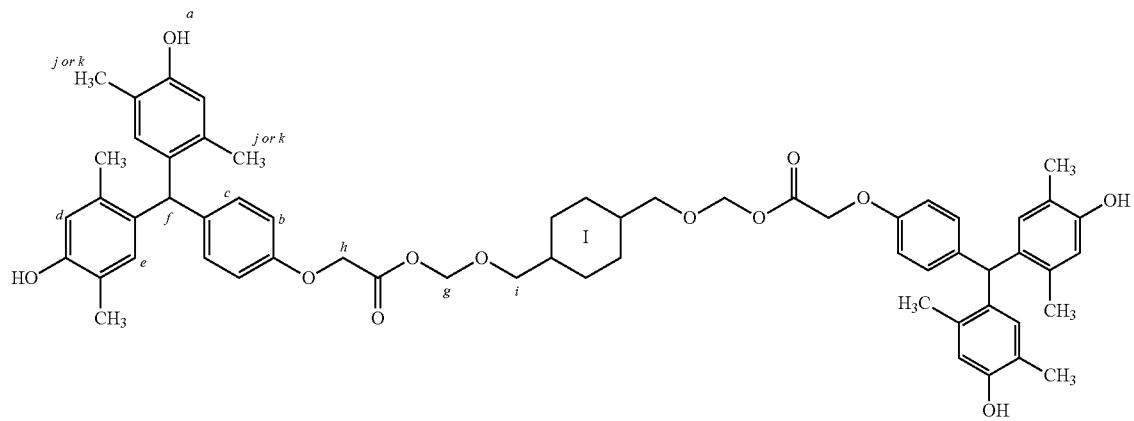

Example 5

Preparation of Resist Composition Comprising Compound (13), and Evaluation Thereof 100 parts by mass of the compound (13) as synthesized in Synthesis Example 10, 10 parts by mass of triphenylsulfonium nonafluorobutanesulfonate, and 1.0 part by mass of tri-n-octyl amine were dissolved in 1370 parts by mass of a mixed solvent of PGMEA and EL (mass ratio: 6:4) to prepare a resist composition.

The positive type resist composition was uniformly applied onto an 8-inch silicon wafer which had been treated with hexamethyldisilazane by using a spinner, and subject to PAB at 110° C. for 90 seconds to form a resist film (film thickness: 150 nm).

Figure 2:
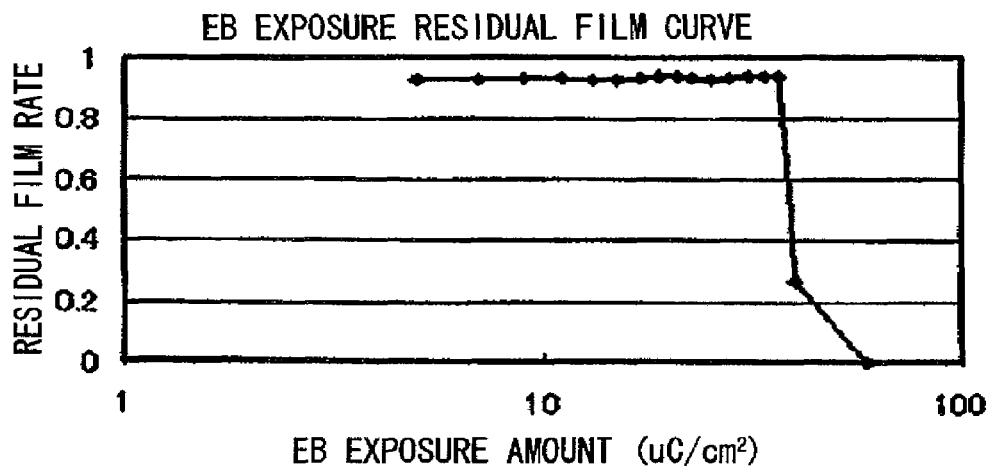
FIG. 2 is a curve of the residual film after EB exposure, showing the change in the residual film rate at varying exposure amounts of EB in the positive type resist composition including the compound of the present invention.

The resist film was exposed (each 1 μm) using an electron beam drawing device HL-800D (VSB) (manufactured by HITACH, Ltd.) at an accelerated voltage of 70 kV, subject to post exposure bake (PEB) at 110° C. for 90 seconds, and subject to developing using an aqueous solution of tetramethylammonium hydroxide (TMAH) at a concentration of 0.5% by mass (23° C.) for 60 seconds. The change in the residual film rates (the film thickness after developing/the film thickness upon formation of a film (before exposure)) by the change in the exposure amounts (EB exposure amount, μC/cm$^2$) of electron beam (EB) was determined to obtain a curve for a residual film (FIG. 2).

From the results, it was confirmed that the resist composition including the compound of the present invention exhibits good contrast.

INDUSTRIAL APPLICABILITY

According to the present invention, there can be provided a positive type resist composition and a method of forming a resist pattern for forming a high resolution resist pattern, using a low-molecular-weight material as a base component; and a compound and a dissolution inhibitor which are each suitably used for the positive type resist composition. Therefore, the present invention is industrially useful.

What is claimed is:

1. A positive type resist composition comprising a base component (A) that increases its own alkali solubility through the action of an acid, and an acid generator component (B) that generates an acid upon irradiation with radiation, wherein the base component (A) contains a compound (A1) that is a non-polymer having a molecular weight of 500 to 3000, and is decomposed under the action of an acid to produce two or more molecules of a decomposition product having a molecular weight of 200 or more, wherein the compound (A1) is a compound (A1-1) represented by the following general formula (A-1) or (A-2), and wherein the proportion of the compound (A1) in the component (A) is in the range of more than 80 to 100% by weight:

[Chemical Formula 3]

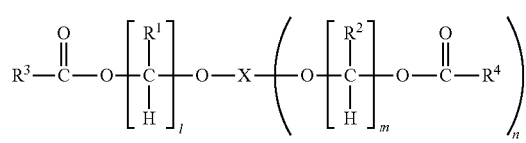

(A-1)

(wherein R$^1$ and R$^2$ are each independently a hydrogen atom; R$^3$ and R$^4$ are each independently a group containing a polycyclic group, or a group containing at least two cyclic groups including at least one aromatic monocyclic group; l and m are each independently an integer of 1 to 3; n is an integer of 1 to 3; and X is an (n+1)-valent organic group)

[Chemical Formula 4]

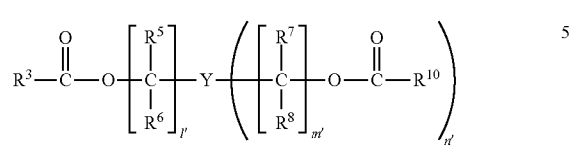

(A-2)

(wherein $R^5$ to $R^8$ are each independently an alkyl group or a halogenated alkyl group; $R^9$ and $R^{10}$ are each independently a group containing a polycyclic group, or a group containing at least two cyclic groups including at least one aromatic monocyclic group; l', and m' are each independently an integer of 1 to 3; n' is an integer of 1 to 3; and Y is an (n'+1)-valent organic group).

* * * * *